(12) United States Patent
Nakamura et al.

(10) Patent No.: US 8,609,847 B2
(45) Date of Patent: Dec. 17, 2013

(54) DIHYDROQUINOLINONE DERIVATIVES

(75) Inventors: Toshio Nakamura, Toshima-ku (JP); Seiji Masuda, Toshima-ku (JP); Aya Futamura, Toshima-ku (JP)

(73) Assignee: Taisho Pharmaceutical Co., Ltd, Tokyo (JP)

( * ) Notice: Subject to any disclaimer, the term of this patent is extended or adjusted under 35 U.S.C. 154(b) by 160 days.

(21) Appl. No.: 13/144,591

(22) PCT Filed: Feb. 5, 2010

(86) PCT No.: PCT/JP2010/052114
§ 371 (c)(1),
(2), (4) Date: Jul. 14, 2011

(87) PCT Pub. No.: WO2010/090347
PCT Pub. Date: Aug. 12, 2010

(65) Prior Publication Data
US 2012/0022064 A1    Jan. 26, 2012

(30) Foreign Application Priority Data

Feb. 6, 2009  (JP) ................. 2009-025462
Jun. 19, 2009  (JP) ................. 2009-146735

(51) Int. Cl.
*C07D 215/38*    (2006.01)
(52) U.S. Cl.
USPC .......................................... 546/159
(58) Field of Classification Search
USPC .......................................... 546/159; 514/312
See application file for complete search history.

(56) References Cited

U.S. PATENT DOCUMENTS

| 4,914,094 | A |   | 4/1990 | Oshiro et al. |
| 5,008,274 | A |   | 4/1991 | Nishi et al. |
| 5,434,164 | A |   | 7/1995 | Nishi et al. |
| 5,786,367 | A | * | 7/1998 | Oshiro et al. ............... 514/312 |
| 2007/0105834 | A1 |   | 5/2007 | Diaz Martin et al. |
| 2008/0269287 | A1 |   | 10/2008 | Ohtake et al. |

FOREIGN PATENT DOCUMENTS

| JP | 62-135423 | A |   | 6/1987 |
| JP | 63-045220 | A |   | 2/1988 |
| JP | 63-290821 | A |   | 11/1988 |
| JP | 2007/001944 |   | * | 1/2007 |
| WO | 2004/026837 | A2 |   | 4/2004 |
| WO | 2005/097751 | A2 |   | 10/2005 |
| WO | 2005/097778 | A1 |   | 10/2005 |
| WO | 2005/118547 | A1 |   | 12/2005 |
| WO | 2006/014136 | A1 |   | 2/2006 |
| WO | 2006/045416 | A1 |   | 5/2006 |
| WO | 2006/046131 | A1 |   | 5/2006 |
| WO | 2006/059778 | A1 |   | 6/2006 |
| WO | 2006/061193 | A1 |   | 6/2006 |
| WO | 2006/103057 | A1 |   | 10/2006 |
| WO | 2006/107661 | A1 |   | 10/2006 |

OTHER PUBLICATIONS

Passani, JPET vol. 336, pp. 24-29, 2011.*
Kukko-Lukjanov, J Neuroscience, Jan. 25, 2006, vol. 26(4), pp. 1088-1097.*
International Search Report PCT/JP2010/052114, Apr. 6, 2010.

* cited by examiner

*Primary Examiner* — D M Seaman
(74) *Attorney, Agent, or Firm* — Sughrue Mion, PLLC

(57) ABSTRACT

The present invention provides a prophylactic or therapeutic agent for dementia, Alzheimer's disease, attention-deficit hyperactivity disorder, schizophrenia, eating disorders, obesity, diabetes, hyperlipidemia, sleep disorders, narcolepsy, sleep apnea syndrome, circadian rhythm disorder, depression, allergic rhinitis or other diseases.
A dihydroquinolinone derivative represented by formula (1) or a pharmaceutically acceptable salt thereof:

[Formula 1]

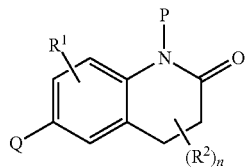

(1)

{wherein Q represents the following formula (A) or (B)}

[Formula 2]

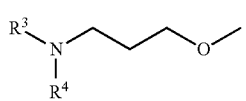

(A)

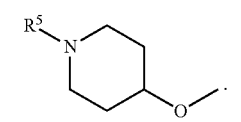

(B)

4 Claims, No Drawings

DIHYDROQUINOLINONE DERIVATIVES

CROSS REFERENCE TO RELATED APPLICATIONS

This application is a National Stage of International Application No. PCT/JP2010/052114 filed Feb. 5, 2010, claiming priorities based on Japanese Patent Application Nos. 2009-25462 filed Feb. 6, 2009 and 2009-146735 filed Jun. 19, 2009, the contents of all of which are incorporated herein by reference in their entirety.

BACKGROUND ART

Histamine is usually stored within intracellular granules in mast cells, lung, liver and gastric mucosa, etc. In response to external stimuli such as antigen binding to cell surface antibody, histamine is released into the extracellular environment. For example, when mast cells are stimulated by an antigen entering from outside, histamine is released from the mast cells and stimulates histamine H1 (H1) receptors located on blood vessels or smooth muscle to cause allergic reactions. Likewise, histamine released from ECL cells (enterochromaffin-like cells) on the gastric mucosa stimulates histamine H2 (H2) receptors on the parietal cells to promote gastric acid secretion. Based on these facts, H1 and H2 receptor antagonists have been developed as therapeutic agents for allergic diseases and gastric ulcer, respectively, both of which are now used widely as medicaments.

Further, it has been elucidated that histamine serves as a neurotransmitter and acts on histamine receptors (histamine H3 (H3) receptors) located in central and peripheral nerves to thereby exert various physiological functions. This receptor was cloned in 1999 and determined for its gene sequence and amino acid sequence. However, its amino acid sequence homology was as low as 22% and 21.4% with H1 receptor and H2 receptor, respectively (see Non-patent Literature 1). H3 receptors are present in the presynaptic membrane and are shown to serve as autoreceptors controlling the synthesis and release of histamine (see Non-patent Literature 2). Moreover, H3 receptors are also shown to control not only the release of histamine, but also the release of other neurotransmitters including acetylcholine, serotonin, dopamine and noradrenaline (see Non-patent Literature 3). These facts suggest that selective H3 receptor modulators may serve as therapeutic agents for various diseases related to abnormal release of neurotransmitters in the nerves.

In fact, the results of animal model studies using synthetic compounds indicate a possibility that H3 receptor antagonists or inverse agonists can be used as therapeutic agents for dementia, Alzheimer's disease (see Non-patent Literatures 4 and 5), attention-deficit hyperactivity disorder (see Non-patent Literature 6), schizophrenia (see Non-patent Literature 7), epilepsy, central convulsion, etc.

Moreover, it is shown that H3 receptors are involved in eating behavior (see Non-patent Literature 8); and hence possible target diseases for H3 receptor antagonists or inverse agonists also include metabolic diseases such as eating disorders, obesity, diabetes, hyperlipidemia, etc.

Further, it is shown that histamine regulates the circadian rhythm in the brain and is responsible for maintaining a balance between waking and sleeping states (see Non-patent Literatures 9 and 10); and hence possible target diseases for H3 receptor antagonists or inverse agonists also include sleep disorders and diseases associated with sleep disorders such as narcolepsy, sleep apnea syndrome, circadian rhythm disorder, depression, etc.

Furthermore, it is shown that H3 receptors are present in sympathetic nerves on the nasal mucosa, and there is a report showing that the combined use of H3 and H1 receptor antagonists remarkably improves nasal congestion (see Non-patent Literature 11). This indicates a possibility that H3 receptor antagonists or inverse agonists are useful for treatment of allergic rhinitis or other diseases, either alone or in combination with H1 receptor antagonists.

H3 receptor antagonists or inverse agonists have been summarized in several reviews (see Non-patent Literatures 12 to 15), and reference may be made to these reviews. In the early years, many reports were issued for imidazole compounds starting from histamine itself as a leading compound. However, these compounds have not yet been developed as medicaments because they are feared to have negative effects such as inhibition of a drug-metabolizing enzyme, cytochrome P450 (CYP).

In recent years, many documents and patents have been reported for non-imidazole H3 receptor antagonists or inverse agonists (see Patent Literatures 1 to 10).

Moreover, histamine H3 receptor antagonists having a dihydroquinolinone structure have also been reported (see Patent Literature 11). However, there is no report about compounds having the structure disclosed in the present invention. As to compounds having a dihydroquinolinone skeleton, hypoxia improvers, platelet adhesion inhibitors and antiarrhythmic agents have been reported (see Patent Literatures 12 to 14). However, there is no disclosure about their affinity for H3 receptors or their selectivity toward histamine receptor subtypes.

CITATION LIST

Patent Literature

[PTL 1] International Patent Publication No. WO2005/097751
[PTL 2] International Patent Publication No. WO2005/097778
[PTL 3] International Patent Publication No. WO2005/118547
[PTL 4] International Patent Publication No. WO2006/014136
[PTL 5] International Patent Publication No. WO2006/045416
[PTL 6] International Patent Publication No. WO2006/046131
[PTL 7] International Patent Publication No. WO2006/059778
[PTL 8] International Patent Publication No. WO2006/061193
[PTL 9] International Patent Publication No. WO2006/107661
[PTL 10] International Patent Publication No. WO2006/103057
[PTL 11] International Patent Publication No. WO2004/026837
[PTL 12] JP 62-135423 A
[PTL 13] JP 63-045220 A
[PTL 14] JP 63-290821 A

Non Patent Literature

[NPL 1] Lovenberg T. W. et al., Molecular pharmacology, 55, 1101-1107, 1999
[NPL 2] Arrang J-M. et al., Nature, 302, 832-837, 1983

[NPL 3] Brown R. E. et al., Progress in Neurobiology, 63, 637-672, 2001

[NPL 4] Huang Y-W. et al., Behavioural Brain Research, 151, 287-293, 2004

[NPL 5] Komater V. A. et al., Behavioural Brain Research, 159, 295-300, 2005

[NPL 6] Passani M. B. et al., Neuroscience and Biobehavioral Reviews, 24, 107-113, 2000

[NPL 7] Fox G. B. et al., J. Pharmacol. Exp. Ther., 313, 176-190, 2005

[NPL 8] Hancock A. A. et al., Curr. Opin. Investig. Drug, 4, 1190-1197

[NPL 9] Huang Z-L. et al., Prog. Natr. Acad. Sci., 103, 4687-4692, 2006

[NPL 10] Babier A. J. et al., Br. J. Pharmacol., 143, 649-661, 2004

[NPL 11] McLeod R. L. et al., Am. J. Rhinol, 13, 391-399, 1999

[NPL 12] Schwartz J. C. et al., Trends in Pharmacol. Sci., 7, 24-28, 1986

[NPL 13] Passani M. B. et al., Trends in Pharmacol. Sci., 25, 618-625, 2004

[NPL 14] Leurs R. et al., Nature Drug Discovery, 4, 107-122, 2005

[NPL 15] Leurs R. et al., Drug Discovery Today, 10, 1613-1627, 2005

SUMMARY OF INVENTION

Technical Problem

The object of the present invention is to find prophylactic or therapeutic agents for histamine H3 receptor-mediated disorders such as dementia, Alzheimer's disease, attention-deficit hyperactivity disorder, schizophrenia, epilepsy, central convulsion, eating disorders, obesity, diabetes, hyperlipidemia, sleep disorders, narcolepsy, sleep apnea syndrome, circadian rhythm disorder, depression, allergic rhinitis or other diseases, wherein the prophylactic or therapeutic agents have a strong inhibitory effect against histamine binding to histamine H3 receptors.

Solution to Problem

As a result of extensive and intensive efforts made to achieve the above object, the inventors of the present invention have found that dihydroquinolinone derivatives have strong inhibitory activity against histamine binding to histamine H3 receptors. This finding led to the completion of the present invention.

Namely, the present invention is directed to the following.

(I) A dihydroquinolinone derivative represented by formula (1) or a pharmaceutically acceptable salt thereof:

[Formula 1]

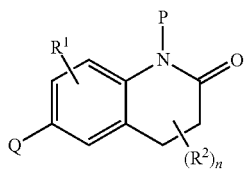

(1)

[wherein Q represents the following formula (A) or (B):

[Formula 2]

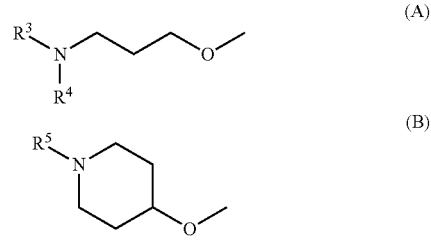

$R^1$ represents a hydrogen atom, a halogen atom or $C_1$-$C_6$ alkyl, $R^2$ represents a hydrogen atom or $C_1$-$C_6$ alkyl, n represents 1 or 2, $R^3$ and $R^4$, which may be the same or different, each represent $C_1$-$C_6$ alkyl or $C_3$-$C_7$ cycloalkyl, or $R^3$ and $R^4$ are attached to each other together with their adjacent nitrogen atom to form a 3- to 7-membered saturated heterocyclic ring (wherein said saturated heterocyclic ring may be substituted with one or two $C_1$-$C_6$ alkyls), $R^5$ represents $C_1$-$C_6$ alkyl (wherein said $C_1$-$C_6$ alkyl may be substituted with one or two $C_3$-$C_7$ cycloalkyls) or $C_3$-$C_7$ cycloalkyl (wherein said $C_3$-$C_7$ cycloalkyl may be substituted with one or two $C_1$-$C_6$ alkyls), and P represents aryl, heteroaryl or heterocyclyl {wherein said aryl, heteroaryl or heterocyclyl may be substituted with the same or different 1 to 3 substituents selected from:

a halogen atom, $C_1$-$C_6$ alkyl (wherein said $C_1$-$C_6$ alkyl may be substituted with 1 to 3 halogen atoms, hydroxys, $C_1$-$C_6$ alkoxys or $C_2$-$C_{12}$ dialkylaminos), $C_1$-$C_6$ alkoxy (wherein said $C_1$-$C_6$ alkoxy may be substituted with 1 to 3 halogen atoms), amino, $C_1$-$C_6$ alkylamino, $C_2$-$C_{12}$ dialkylamino, $C_2$-$C_7$ alkanoyl, $C_4$-$C_8$ cycloalkylcarbonyl, cyano, $C_2$-$C_7$ alkoxycarbonyl, $C_2$-$C_7$ alkylaminocarbonyl, $C_3$-$C_{13}$ dialkylaminocarbonyl, carbonyl attached to a monocyclic saturated heterocyclic ring which contains one or more nitrogen atoms in the ring and may further contain an oxygen or sulfur atom, carbamoyl, heteroaryl, heterocyclyl (wherein said heterocyclyl may be substituted with one or two $C_1$-$C_6$ alkyls), or heteroaryloxy (wherein said heteroaryloxy may be substituted with one or two $C_1$-$C_6$ alkyls)}].

(II) The dihydroquinolinone derivative or pharmaceutically acceptable salt thereof according to (I) above, wherein formula (1) is represented by formula (2):

[Formula 3]

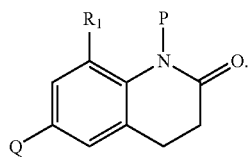

(2)

(III) The dihydroquinolinone derivative or pharmaceutically acceptable salt thereof according to (I) or (II) above, wherein P represents phenyl, pyridyl, pyrimidinyl, quinolinyl, naphthyridyl, indolyl, 2,3-dihydro[1,4]benzodioxinyl, benzo[1,3]dioxolyl, 2,3-dihydrobenzofuranyl or 2-oxo-1,2-dihydropyridinyl {wherein said phenyl, pyridyl, pyrimidinyl, quinolinyl, naphthyridyl, indolyl, 2,3-dihydro[1,4]benzodioxinyl, benzo[1,3]dioxolyl, 2,3-dihydrobenzofuranyl or 2-oxo-1,2-dihydropyridinyl may be substituted with the same or different 1 to 3 substituents selected from:

a halogen atom, $C_1$-$C_6$ alkyl (wherein said $C_1$-$C_6$ alkyl may be substituted with 1 to 3 halogen atoms, hydroxys, $C_1$-$C_6$ alkoxys or $C_2$-$C_{12}$ dialkylaminos), $C_1$-$C_6$ alkoxy (wherein said $C_1$-$C_6$ alkoxy may be substituted with 1 to 3 halogen atoms), $C_2$-$C_7$ alkanoyl, $C_4$-$C_8$ cycloalkylcarbonyl, cyano, $C_2$-$C_7$ alkoxycarbonyl, $C_2$-$C_7$ alkylaminocarbonyl, $C_3$-$C_{13}$ dialkylaminocarbonyl, pyrrolidin-1-ylcarbonyl, carbamoyl, oxazolyl, morpholin-4-yl or 2-oxopyrrolidin-1-yl (wherein said morpholin-4-yl or 2-oxopyrrolidin-1-yl may be substituted with one or two $C_1$-$C_6$ alkyls), or pyridazinyloxy (wherein said pyridazinyloxy may be substituted with one or two $C_1$-$C_6$ alkyls)}.

(IV) A pharmaceutical preparation, which comprises the dihydroquinolinone derivative or pharmaceutically acceptable salt thereof according to any one of (I) to (III) above as an active ingredient.

(V) A prophylactic or therapeutic agent for dementia, Alzheimer's disease, attention-deficit hyperactivity disorder, schizophrenia, epilepsy, central convulsion, eating disorders, obesity, diabetes, hyperlipidemia, sleep disorders, narcolepsy, sleep apnea syndrome, circadian rhythm disorder, depression or allergic rhinitis, which comprises the dihydroquinolinone derivative or pharmaceutically acceptable salt thereof according to any one of (I) to (III) above as an active ingredient.

Advantageous Effects of Invention

The compounds of the present invention were found to have an excellent histamine H3 receptor antagonistic effect.

DESCRIPTION OF EMBODIMENTS

The terms and expressions used herein are defined as follows.

As used herein, the term "halogen atom" refers to a fluorine atom, a chlorine atom, a bromine atom or an iodine atom.

The term "$C_1$-$C_6$ alkyl" refers to a linear or branched alkyl group containing 1 to 6 carbon atoms. Examples include methyl, ethyl, n-propyl, isopropyl, n-butyl, isobutyl, sec-butyl, tert-butyl, n-pentyl, isopentyl, neopentyl and n-hexyl groups.

The term "$C_3$-$C_7$ cycloalkyl" refers to a cyclopropyl, cyclobutyl, cyclopentyl, cyclohexyl or cycloheptyl group.

The term "$C_1$-$C_6$ alkoxy" refers to a linear or branched alkoxy group containing 1 to 6 carbon atoms. Examples include methoxy, ethoxy, n-propoxy, isopropoxy, n-butoxy, isobutoxy, sec-butoxy, tert-butoxy, n-pentyloxy, isopentyloxy, neopentyloxy and n-hexyloxy groups.

The term "$C_2$-$C_7$ alkoxycarbonyl" refers to a carbonyl group attached to a linear or branched alkoxy group containing 1 to 6 carbon atoms. Examples include methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl, n-pentyloxycarbonyl, isopentyloxycarbonyl, neopentyloxycarbonyl and n-hexyloxycarbonyl groups.

The term "$C_1$-$C_6$ alkylamino" refers to an amino group substituted with a linear or branched alkyl group containing 1 to 6 carbon atoms. Examples include methylamino, ethylamino, n-propylamino, isopropylamino, n-butylamino, isobutylamino, sec-butylamino, tert-butylamino, n-pentylamino, isopentylamino, neopentylamino and n-hexylamino groups.

The term "$C_2$-$C_{12}$ dialkylamino" refers to an amino group substituted with two linear or branched alkyl groups each containing 1 to 6 carbon atoms. Examples include dimethylamino, diethylamino, di-n-propylamino, N,N-isopropylmethylamino, di-n-butylamino, diisobutylamino, N,N-sec-butylethylamino, N,N-tert-butylmethylamino, di-n-pentylamino, N,N-isopentylmethylamino, N,N-neopentylmethylamino and di-n-hexylamino groups.

The term "$C_2$-$C_7$ alkanoyl" refers to a carbonyl group attached to an alkyl group containing 1 to 6 carbon atoms. Examples include acetyl, propionyl, butyryl, isobutyryl, pivaloyl, pentanoyl, 3-methylbutyryl, 4,4-dimethylpentanoyl and heptanoyl groups.

The term "$C_4$-$C_8$ cycloalkylcarbonyl" refers to a cyclopropanecarbonyl, cyclobutanecarbonyl, cyclopentanecarbonyl, cyclohexanecarbonyl or cycloheptanecarbonyl group.

The term "$C_2$-$C_7$ alkylaminocarbonyl" refers to a carbonyl group attached to a linear or branched alkylamino group containing 1 to 6 carbon atoms. Examples include methylaminocarbonyl, ethylaminocarbonyl, n-propylaminocarbonyl, isopropylaminocarbonyl, n-butylaminocarbonyl, isobutylaminocarbonyl, sec-butylaminocarbonyl, tert-butylaminocarbonyl, n-pentylaminocarbonyl, isopentylaminocarbonyl, neopentylaminocarbonyl and n-hexylaminocarbonyl groups.

The term "$C_3$-$C_{13}$ dialkylaminocarbonyl" refers to a carbonyl group attached to a dialkylamino group containing 2 to 12 carbon atoms. Examples include dimethylaminocarbonyl, diethylaminocarbonyl, di-n-propylaminocarbonyl, N,N-isopropylmethylaminocarbonyl, di-n-butylaminocarbonyl, diisobutylaminocarbonyl, N,N-sec-butylethylaminocarbonyl, N,N-tert-butylmethylaminocarbonyl, di-n-pentylaminocarbonyl, N,N-isopentylmethylaminocarbonyl, N,N-neopentylmethylaminocarbonyl and di-n-hexylaminocarbonyl groups.

The expression "carbonyl attached to a monocyclic saturated heterocyclic ring which contains one or more nitrogen atoms in the ring and may further contain an oxygen or sulfur atom" is intended to mean a carbonyl group attached to a saturated 3- to 7-membered monocyclic heterocyclic ring which contains one or more nitrogen atoms in the ring and may further contain one or more additional heteroatoms selected from nitrogen, oxygen and sulfur atoms. Examples include aziridin-1-ylcarbonyl, azetidin-1-ylcarbonyl, pyrrolidin-1-ylcarbonyl, piperidin-1-ylcarbonyl, azepan-1-ylcarbonyl, imidazolidin-1-ylcarbonyl, pyrazolidin-1-ylcarbonyl, piperazin-1-ylcarbonyl, oxazolidin-1-ylcarbonyl, morpholin-1-ylcarbonyl and thiomorpholin-1-ylcarbonyl groups.

The expression "attached to each other together with their adjacent nitrogen atom to form a 3- to 7-membered saturated heterocyclic ring" is intended to mean a 1-aziridinyl, 1-azetidinyl, 1-pyrrolidinyl, piperidino or 1-azepanyl group.

The term "aryl" refers to a mono- to tetracyclic aromatic carbocyclic group composed of 6 to 18 carbon atoms. Examples include a phenyl group, a naphthyl group, an anthryl group, a phenanthrenyl group, a tetracenyl group and a pyrenyl group.

The term "heteroaryl" refers to a group composed of a 5- or 6-membered monocyclic or 9- or 10-membered bicyclic aromatic heterocyclic ring. Examples include pyridyl, pyridazinyl, pyrimidinyl, pyrazinyl, quinolinyl, isoquinolinyl, quinazolinyl, quinoxalinyl, naphthylizinyl, pyrrolyl, furanyl, thiophenyl, pyrazolyl, imidazolyl, oxazolyl, isoxazolyl, thiazolyl, isothiazolyl, triazolyl, indolyl, benzofuranyl, benzothiophenyl, benzoimidazolyl, indazolyl, benzoxazolyl, benzothiazolyl and benzotriazolyl groups. More specific examples include 2-pyridyl, 3-pyridyl, 4-pyridyl, pyridazin-3-yl, pyridazin-4-yl, pyrimidin-2-yl, pyrimidin-4-yl, pyrimidin-5-yl, pyrazin-2-yl, quinolin-2-yl, quinolin-3-yl, quinolin-4-yl, quinolin-6-yl, quinolin-8-yl, isoquinolin-1-yl, isoquinolin-6-yl, quinazolin-2-yl, quinazolin-5-yl, quinoxalin-2-yl, quinoxalin-6-yl, 1,5-naphthylizin-3-yl, 1,6-naphthylizin-8-yl, pyrrol-3-yl, furan-2-yl, furan-3-yl, thiophen-2-yl, thiophen-3-yl, pyrazol-3-yl, pyrazol-4-yl, imidazol-2-yl, oxazol-2-yl, oxazol-4-yl, oxazol-5-yl, isoxazol-3-yl, thiazol-2-yl, thiazol-5-yl, isothiazol-4-yl, 1,2,4-triazol-3-yl, indol-2-yl, indol-3-yl, indol-5-yl, indol-7-yl, benzofuran-3-yl, benzothiophen-3-yl, benzoimidazol-2-yl, indazol-5-yl, benzoxazol-2-yl, benzothiazol-2-yl and benzotriazol-4-yl groups.

The term "heterocyclyl" refers to a group composed of a 5- or 6-membered monocyclic or 9- or 10-membered bicyclic saturated heterocyclic ring, which contains one or more nitrogen, oxygen and sulfur atoms in the ring and may contain an unsaturated bond as a part of the ring. Heterocyclyl may be substituted with one or two oxo groups. Examples include 1-pyrrolidinyl, 1-piperidinyl, 1-piperazinyl, morpholin-4-yl, thiomorpholin-4-yl, 2-oxopyrrolidin-1-yl, 2,5-dioxopyrrolidin-1-yl, 2-tetrahydrofuranyl, 3-tetrahydrofuranyl, 4-tetrahydropyranyl, 1,4,5,6-tetrahydropyridazin-3-yl, 2-oxo-1,2-dihydropyridin-4-yl, indolin-4-yl, indolin-6-yl, isoindolin-4-yl, 1,2,3,4-tetrahydroquinolin-7-yl, 1,2,3,4-tetrahydroisoquinolin-6-yl, 2,3-dihydrobenzofuran-5-yl, 2,3-dihydrobenzofuran-6-yl, benzo[1,3]dioxol-5-yl, 2,3-dihydro[1,4]benzodioxin-5-yl, 2,3-dihydro[1,4]benzodioxin-6-yl and 3,4-dihydro[1,4]benzoxazin-7-yl groups.

The term "heteroaryloxy" refers to a group in which "heteroaryl" as defined above is attached via an oxygen atom. Examples include pyridyloxy, pyridazinyloxy, pyrimidinyloxy, pyrazinyloxy, quinolinyloxy, isoquinolinyloxy, quinazolinyloxy, quinoxalinyloxy, naphthylizinyloxy, pyrrolyloxy, furanyloxy, thiophenyloxy, pyrazolyloxy, imidazolyloxy, oxazolyloxy, isoxazolyloxy, thiazolyloxy, isothiazolyloxy, triazolyloxy, indolyloxy, benzofuranyloxy, benzothiophenyloxy, benzoimidazolyloxy, indazolyloxy, benzoxazolyloxy, benzothiazolyloxy and benzotriazolyloxy groups. More specific examples include pyridin-2-yloxy, pyridin-3-yloxy, pyridin-4-yloxy and pyridazin-3-yloxy groups.

One preferred embodiment of the present invention is a dihydroquinolinone derivative represented by formula (2) or a pharmaceutically acceptable salt thereof:

[Formula 4]

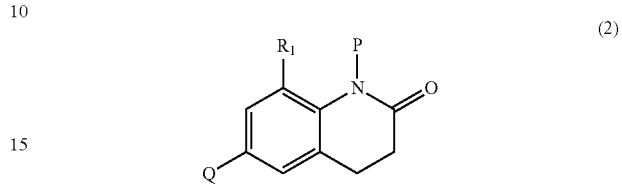

[wherein Q represents the following formula (A) or (B):

[Formula 5]

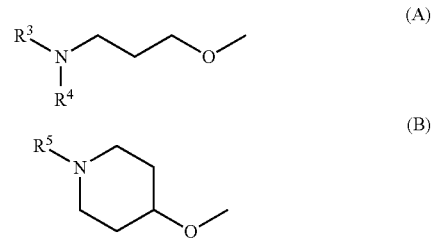

$R^1$ represents a hydrogen atom, a halogen atom or $C_1$-$C_6$ alkyl, $R^3$ and $R^4$, which may be the same or different, each represent $C_1$-$C_6$ alkyl or $C_3$-$C_7$ cycloalkyl, or $R^3$ and $R^4$ are attached to each other together with their adjacent nitrogen atom to form a 3- to 7-membered saturated heterocyclic ring (wherein said saturated heterocyclic ring may be substituted with one or two $C_1$-$C_6$ alkyls), $R^5$ represents $C_1$-$C_6$ alkyl (wherein said $C_1$-$C_6$ alkyl may be substituted with one or two $C_3$-$C_7$ cycloalkyls) or $C_3$-$C_7$ cycloalkyl (wherein said $C_3$-$C_7$ cycloalkyl may be substituted with one or two $C_1$-$C_6$ alkyls), and P represents phenyl, pyridyl, pyrimidinyl, quinolinyl, naphthyridyl, indolyl, 2,3-dihydro[1,4]benzodioxinyl, benzo[1,3]dioxolyl, 2,3-dihydrobenzofuranyl or 2-oxo-1,2-dihydropyridinyl {wherein said phenyl, pyridyl, pyrimidinyl, quinolinyl, naphthyridyl, indolyl, 2,3-dihydro[1,4]benzodioxinyl, benzo[1,3]dioxolyl, 2,3-dihydrobenzofuranyl or 2-oxo-1,2-dihydropyridinyl may be substituted with the same or different 1 to 3 substituents selected from:

a halogen atom, $C_1$-$C_6$ alkyl (wherein said $C_1$-$C_6$ alkyl may be substituted with 1 to 3 halogen atoms, hydroxys, $C_1$-$C_6$ alkoxys or $C_2$-$C_{12}$ dialkylaminos), $C_1$-$C_6$ alkoxy (wherein said $C_1$-$C_6$ alkoxy may be substituted with 1 to 3 halogen atoms), $C_2$-$C_7$ alkanoyl, $C_4$-$C_8$ cycloalkylcarbonyl, cyano, $C_2$-$C_7$ alkoxycarbonyl, $C_2$-$C_7$ alkylaminocarbonyl, $C_3$-$C_{13}$ dialkylaminocarbonyl,
pyrrolidin-1-ylcarbonyl,
carbamoyl,
oxazolyl,
morpholin-4-yl or 2-oxopyrrolidin-1-yl (wherein said morpholin-4-yl or 2-oxopyrrolidin-1-yl may be substituted with one or two $C_1$-$C_6$ alkyls), or
pyridazinyloxy (wherein said pyridazinyloxy may be substituted with one or two $C_1$-$C_6$ alkyls)}].

In this case, $R^1$ is preferably a hydrogen atom.

In formula (A), $R^3$ and $R^4$ are preferably attached to each other together with their adjacent nitrogen atom to form a 3- to 7-membered saturated heterocyclic ring (wherein said saturated heterocyclic ring may be substituted with one or two $C_1$-$C_6$ alkyls), more preferably a 1-pyrrolidinyl group (wherein said 1-pyrrolidinyl group may be substituted with one or two $C_1$-$C_6$ alkyls).

P is preferably a phenyl or pyridyl group {wherein said phenyl or pyridyl group may be substituted with the same or different 1 to 3 substituents selected from:
a halogen atom,
$C_1$-$C_6$ alkyl (wherein said $C_1$-$C_6$ alkyl may be substituted with 1 to 3 halogen atoms, hydroxys, $C_1$-$C_6$ alkoxys or $C_2$-$C_{12}$ dialkylaminos),
$C_1$-$C_6$ alkoxy (wherein said $C_1$-$C_6$ alkoxy may be substituted with 1 to 3 halogen atoms),
$C_2$-$C_7$ alkanoyl,
$C_4$-$C_8$ cycloalkylcarbonyl,
cyano,
$C_2$-$C_7$ alkoxycarbonyl,
$C_2$-$C_7$ alkylaminocarbonyl,
$C_3$-$C_{13}$ dialkylaminocarbonyl,
pyrrolidin-1-ylcarbonyl,
carbamoyl,
oxazolyl,
morpholin-4-yl or 2-oxopyrrolidin-1-yl (wherein said morpholin-4-yl or 2-oxopyrrolidin-1-yl may be substituted with one or two $C_1$-$C_6$ alkyls), or
pyridazinyloxy (wherein said pyridazinyloxy may be substituted with one or two $C_1$-$C_6$ alkyls)}.

P is more preferably a phenyl or pyridyl group {wherein said phenyl or pyridyl group may be substituted with the same or different 1 to 2 substituents selected from:
a halogen atom,
$C_1$-$C_6$ alkyl (wherein said $C_1$-$C_6$ alkyl may be substituted with 1 to 3 halogen atoms, hydroxys, $C_1$-$C_6$ alkoxys or $C_2$-$C_{12}$ dialkylaminos),
$C_1$-$C_6$ alkoxy (wherein said $C_1$-$C_6$ alkoxy may be substituted with 1 to 3 halogen atoms),
$C_2$-$C_7$ alkanoyl,
$C_4$-$C_8$ cycloalkylcarbonyl,
cyano,
$C_2$-$C_7$ alkoxycarbonyl,
$C_2$-$C_7$ alkylaminocarbonyl,
$C_3$-$C_{13}$ dialkylaminocarbonyl, or pyrrolidin-1-ylcarbonyl}.

As used herein, the term "pharmaceutically acceptable salt" is intended to include a salt with an inorganic acid such as sulfuric acid, hydrochloric acid, hydrobromic acid, phosphoric acid or nitric acid; a salt with an organic acid such as acetic acid, oxalic acid, lactic acid, tartaric acid, fumaric acid, maleic acid, citric acid, benzenesulfonic acid, methanesulfonic acid, p-toluenesulfonic acid, benzoic acid, camphorsulfonic acid, ethanesulfonic acid, glucoheptonic acid, gluconic acid, glutamic acid, glycolic acid, malic acid, malonic acid, mandelic acid, galactaric acid or naphthalene-2-sulfonic acid; a salt with one or more metal ions such as lithium ion, sodium ion, potassium ion, calcium ion, magnesium ion, zinc ion and/or aluminum ion; as well as a salt with ammonia or an amine such as arginine, lysine, piperazine, choline, diethylamine, 4-phenylcyclohexylamine, 2-aminoethanol or benzathine.

The compounds of the present invention may be present in the form of various solvates. They may also be in hydrate form in terms of applicability as pharmaceutical preparations.

The compounds of the present invention encompass all of the following: enantiomers, diastereomers, equilibrium compounds, mixtures thereof at any ratio, racemates, etc.

The compounds of the present invention also encompass compounds in which one or more hydrogen atoms, carbon atoms, nitrogen atoms, oxygen atoms or sulfur atoms are replaced by their radioisotopes or stable isotopes. These labeled compounds are useful for metabolism and/or pharmacokinetics study, biological analysis as receptor ligands, or other purposes.

The compounds of the present invention may be formulated into pharmaceutical preparations in combination with one or more pharmaceutically acceptable carriers, excipients or diluents. Examples of such carriers, excipients and diluents include water, lactose, dextrose, fructose, sucrose, sorbitol, mannitol, polyethylene glycol, propylene glycol, starch, gum, gelatin, alginate, calcium silicate, calcium phosphate, cellulose, water syrup, methylcellulose, polyvinylpyrrolidone, alkyl parahydroxy benzosorbate, talc, magnesium stearate, stearic acid, glycerine, as well as various oils such as sesame oil, olive oil, soybean oil, and the like.

Moreover, the above carriers, excipients or diluents may optionally be blended with commonly used additives such as extenders, binders, disintegrating agents, pH adjustors, solubilizers and so on, and then formulated using standard techniques into oral or parenteral dosage forms including tablets, pills, capsules, granules, powders, solutions, emulsions, suspensions, ointments, injections, skin plasters, etc. The compounds of the present invention may be given to adult patients at 0.001 to 500 mg per administration, once or several times a day, by the oral or parenteral route. This dosage may be increased or decreased as appropriate for the type of disease to be treated, the age, body weight and symptom of a patient, etc.

Profiles desired for the compounds of the present invention include excellent efficacy, good in vivo kinetics (good oral absorption, no tissue-specific accumulation), excellent physical properties, low toxicity, etc. Preferred compounds of the present invention are expected to have an excellent ability to penetrate into the brain.

The compounds of the present invention can be prepared in the following manner.

The compounds of the present invention can be prepared by known organic chemistry procedures, for example, according to the following reaction schemes. In Reaction Schemes 1 to 4 shown below, $R^1$, $R^2$, $R^3$, $R^4$, $R^5$, n and P are as defined above. $R^6$ represents a hydrogen atom or a group commonly used as a protecting group for a hydroxyl group (e.g., acetyl, benzoyl, benzyl, benzyloxycarbonyl, tert-butoxycarbonyl, methoxymethyl, tetrahydropyranyl or tert-butyldimethylsilyl), $R^7$ and $R^8$ each represent a hydrogen atom, an alkyl group or a cycloalkyl group, or alternatively, $R^7$ and $R^8$ may form cycloalkyl together with their adjacent carbon atom, $X^1$ and $X^2$, which may be the same or different, each represent a leaving group such as a halogen atom (e.g., a chlorine atom, a bromine atom, an iodine atom) or an organic sulfonyloxy group (e.g., a methanesulfonyloxy group, a phenylsulfonyloxy group, a p-toluenesulfonyloxy group, a trifluoromethanesulfonyloxy group), $Y^1$, $Y^2$, $Y^3$ and $Y^4$, which may be the same or different, each represent a leaving group (e.g., a halogen atom or an organic sulfonyloxy group) or a hydroxyl group, and the dotted line represents a single bond or a double bond.

Explanation will be given below of the process shown in Reaction Scheme 1 for preparing the compound of the present invention. This process is intended to prepare the compound (1-2) of the present invention from compound (2).

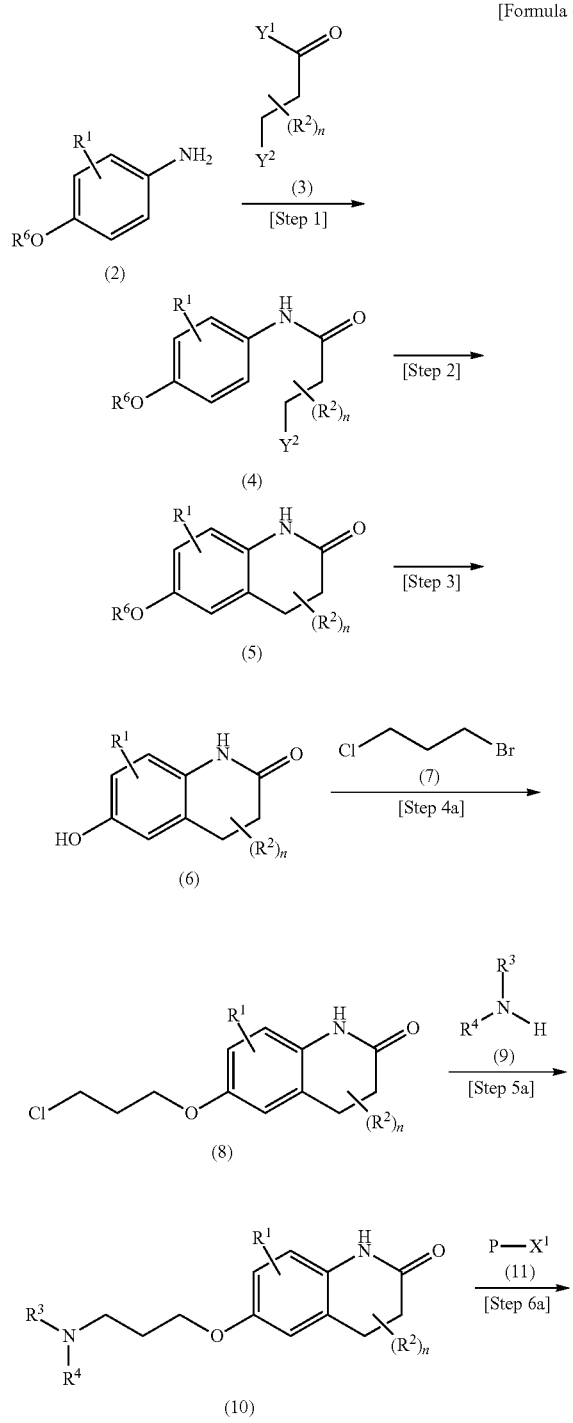

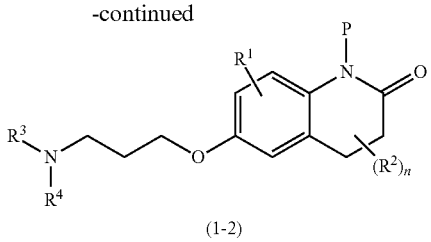

(Step 1)

Step 1 is intended to obtain compound (4) by condensation between compounds (2) and (3) through coupling reaction. Compounds (2) and (3) are known or may be easily synthesized from known compounds.

In a case where $Y^1$ is a hydroxyl group, the reaction may be accomplished by standard procedures for amidation of carboxylic acids, for example, through conversion of a carboxylic acid into a carboxylic acid halide (e.g., carboxylic acid chloride, carboxylic acid bromide) and the subsequent reaction with an amine, through reaction of a mixed acid anhydride (e.g., obtained from a carboxylic acid and a chlorocarbonate ester) with an amine, through conversion of a carboxylic acid into an active ester (e.g., 1-benzotriazolyl ester, succinimidyl ester) and the subsequent reaction with an amine, or through reaction of a carboxylic acid with an amine in the presence of a dehydration condensing agent. All of these reactions may be accomplished in the presence or absence of a base in a solvent. Examples of a dehydration condensing agent available for use in this reaction include 3-(3-dimethylaminopropyl)-1-ethylcarbodiimide hydrochloride, dicyclohexylcarbodiimide, diphenylphosphorylazide, and carbonyldiimidazole. If necessary, it is possible to use an activator such as 1-hydroxybenzotriazole or hydroxysuccinimide. Examples of a base available for use in this reaction include pyridine, triethylamine, diisopropylethylamine, potassium carbonate, sodium carbonate, and sodium bicarbonate. Examples of a solvent available for use in this reaction include ethers (e.g., tetrahydrofuran, 1,2-dimethoxyethane, 1,4-dioxane); hydrocarbons (e.g., toluene, benzene); halogenated hydrocarbons (e.g., chloroform, dichloromethane); amides (e.g., N,N-dimethylformamide, N,N-dimethylacetamide, N-methyl-2-pyrrolidone); ketones (e.g., acetone, 2-butanone); dimethyl sulfoxide; acetonitrile; water; or mixed solvents thereof. The reaction temperature in this reaction generally ranges from 0° C. to 120° C., preferably from 15° C. to 40° C., and the reaction time generally ranges from 1 to 48 hours, preferably from 1 to 16 hours.

In a case where $Y^1$ is a halogen atom, the reaction may be accomplished by reaction between compounds (2) and (3) in the presence or absence of a base with or without a solvent. Examples of a base available for use in this reaction include pyridine, triethylamine, diisopropylethylamine, potassium carbonate, sodium bicarbonate, and sodium hydroxide. Examples of a solvent available for use in this reaction include ethers (e.g., tetrahydrofuran, 1,2-dimethoxyethane, 1,4-dioxane); hydrocarbons (e.g., toluene, benzene); halogenated hydrocarbons (e.g., chloroform, dichloromethane); amides (e.g., N,N-dimethylformamide, N,N-dimethylacetamide, N-methyl-2-pyrrolidone); or mixed solvents thereof. The reaction temperature in this reaction generally ranges from 0° C. to 120° C., preferably from 15° C. to 40° C., and the reaction time generally ranges from 1 to 48 hours, preferably from 1 to 16 hours.

(Step 2)

Step 2 is intended to obtain compound (5) by intramolecular cyclization of compound (4).

In a case where $Y^2$ is a hydroxyl group, the reaction may be accomplished by reaction of compound (4) in the presence of an acid with or without a solvent, for example, according to the method described in Journal of Heterocyclic Chemistry, 1991, vol. 28, p. 919 or equivalent methods thereof. Examples of an acid available for use in this reaction include Lewis acids such as aluminum trichloride, zinc dichloride, boron trifluoride, and titanium tetrachloride; as well as inorganic acids such as sulfuric acid, phosphoric acid, and polyphosphoric acid. Examples of a solvent available for use in this reaction include ethers (e.g., diethyl ether, 1,4-dioxane); aromatic hydrocarbons (e.g., toluene, benzene, nitrobenzene, chlorobenzene); halogenated hydrocarbons (e.g., chloroform, dichloromethane, 1,2-dichloroethane); carbon disulfide; or mixed solvents thereof. The reaction temperature in this reaction generally ranges from 0° C. to 200° C., preferably from 15° C. to 150° C., and the reaction time generally ranges from 1 to 48 hours, preferably from 1 to 16 hours.

In a case where $Y^2$ is a halogen atom, the reaction may be accomplished by reaction of compound (4) in the presence of an acid with or without a solvent, for example, according to the method described in Journal of American Chemical Society, 1973, vol. 95, p. 546 or equivalent methods thereof. Examples of an acid available for use in this reaction include Lewis acids such as aluminum trichloride, zinc dichloride, boron trifluoride, and titanium tetrachloride; as well as inorganic acids such as sulfuric acid, phosphoric acid, and polyphosphoric acid. Examples of a solvent available for use in this reaction include ethers (e.g., diethyl ether, 1,4-dioxane); aromatic hydrocarbons (e.g., toluene, benzene, nitrobenzene, chlorobenzene); halogenated hydrocarbons (e.g., chloroform, dichloromethane, 1,2-dichloroethane); carbon disulfide; or mixed solvents thereof. The reaction temperature in this reaction generally ranges from 0° C. to 200° C., preferably from 15° C. to 150° C., and the reaction time generally ranges from 1 to 48 hours, preferably from 1 to 16 hours.

(Step 3)

Step 3 is intended to obtain compound (6) by deprotection in a case where $R^6$ in compound (5) is a group commonly used as a protecting group for a hydroxyl group. If $R^6$ is a hydrogen atom, this step is not needed. The reaction may be accomplished by standard deprotection reaction as appropriate for the type of protecting group, for example, according to the method described in T. W. Greene and P. G. M. Wuts ed., Protective Groups in Organic Synthesis, third edition, John Wiley and Sons, Inc. or equivalent methods thereof.

(Step 4a)

Step 4a is intended to obtain compound (8) by coupling reaction between compound (6) and known compound (7). The reaction may be accomplished by standard procedures for reaction between phenol and alkyl halide in the presence of a base with or without a solvent. If necessary, for example, an additive such as potassium iodide or sodium bromide may be added. Examples of a base available for use in this reaction include pyridine, triethylamine, diisopropylethylamine, potassium tert-butoxide, potassium carbonate, cesium carbonate, sodium bicarbonate, sodium hydroxide, potassium hydroxide, and sodium hydride. Examples of a solvent available for use in this reaction include alcohols (e.g., methanol, ethanol, isopropanol); ethers (e.g., tetrahydrofuran, 1,2-dimethoxyethane, 1,4-dioxane); hydrocarbons (e.g., toluene, benzene); halogenated hydrocarbons (e.g., chloroform, dichloromethane); amides (e.g., N,N-dimethylformamide, N,N-dimethylacetamide, N-methyl-2-pyrrolidone); ketones (e.g., acetone, 2-butanone); dimethyl sulfoxide; acetonitrile; water; or mixed solvents thereof. The reaction temperature in this reaction generally ranges from 0° C. to 200° C., preferably from 15° C. to 100° C., and the reaction time generally ranges from 1 to 48 hours, preferably from 1 to 16 hours.

(Step 5a)

Step 5a is intended to obtain compound (10) by condensation between compounds (8) and (9) through coupling reaction. Compound (9) is known or may be easily synthesized from a known compound. The reaction may be accomplished by standard procedures for reaction between amine and alkyl halide in the presence or absence of a base with or without a solvent. If necessary, for example, an additive such as potassium iodide or sodium bromide may be added. Examples of a base available for use in this reaction include pyridine, triethylamine, diisopropylethylamine, potassium tert-butoxide, potassium carbonate, cesium carbonate, sodium bicarbonate, sodium hydroxide, potassium hydroxide, and sodium hydride. Examples of a solvent available for use in this reaction include alcohols (e.g., methanol, ethanol, isopropanol); ethers (e.g., tetrahydrofuran, 1,2-dimethoxyethane, 1,4-dioxane); hydrocarbons (e.g., toluene, benzene); halogenated hydrocarbons (e.g., chloroform, dichloromethane); amides (e.g., N,N-dimethylformamide, N,N-dimethylacetamide, N-methyl-2-pyrrolidone); ketones (e.g., acetone, 2-butanone); dimethyl sulfoxide; acetonitrile; water; or mixed solvents thereof. The reaction temperature in this reaction generally ranges from 0° C. to 200° C., preferably from 15° C. to 100° C., and the reaction time generally ranges from 1 to 48 hours, preferably from 1 to 16 hours.

(Step 6a)

Step 6a is intended to obtain the compound (1-2) of the present invention by condensation between compounds (10) and (11) through cross-coupling reaction. Compound (11) is known or may be easily synthesized from a known compound. The reaction may be accomplished by standard procedures in the presence of a catalyst and its ligand in a solvent, for example, according to the method described in Kunz et al., Synlett, 2003, vol. 15, pp. 2428-2439 or equivalent methods thereof. This reaction is preferably performed in the presence of a base. Examples of a catalyst available for use in this reaction include transition metal catalysts commonly used for cross-coupling reaction, as exemplified by copper, nickel and palladium. More specific examples include copper(0), copper (I) iodide, copper(I) chloride, copper(I) oxide, copper(I) bromide tristriphenylphosphine complex, copper(I) trifluoromethanesulfonate benzene complex, palladium(II) acetate, tetrakis(triphenylphosphine)palladium(0), bis(triphenylphosphine)palladium(II) chloride, [1,1'-bis(diphenylphosphino)ferrocene]palladium(II) dichloride, tris(dibenzylideneacetone)dipalladium(0), and bis(acetylacetonato) nickel(II). Examples of a ligand available for use in this reaction include ligands commonly used for condensation reaction in the presence of a metal catalyst, as exemplified by N,N'-dimethylethylenediamine, N,N'-dimethylcyclohexane-1,2-diamine, 2-aminopyridine, 1,10-phenanthroline, 2-hydroxybenzaldehyde oxime, ethylene glycol, triphenylphosphine, and tri-tert-butylphosphine. Examples of a base available for use in this reaction include potassium carbonate, potassium phosphate, potassium hydroxide, potassium tert-butoxide, sodium tert-butoxide, cesium carbonate, sodium carbonate, sodium bicarbonate, sodium acetate, sodium methoxide, and tetrabutylammonium hydroxide. Examples of a solvent available for use in this reaction include alcohols (e.g., methanol, ethanol, isopropanol); ethers (e.g., tetrahydrofuran, 1,2-dimethoxyethane, 1,4-dioxane); hydrocarbons (e.g., toluene, benzene); halogenated hydrocarbons (e.g., chloroform, dichloromethane); amides (e.g., N,N-dimethylformamide, N,N-dimethylacetamide, N-methyl-2-pyrrolidone); ketones (e.g., acetone, 2-butanone); dimethyl sulfoxide; acetonitrile; water; or mixed solvents thereof. The reaction temperature in this reaction generally ranges from 0° C. to 200° C., preferably from 40° C. to 150° C., and the reaction time generally ranges from 1 to 48 hours, preferably from 1 to 16 hours.

Alternatively, compound (5) can also be prepared according to the process shown in Reaction Scheme 2.

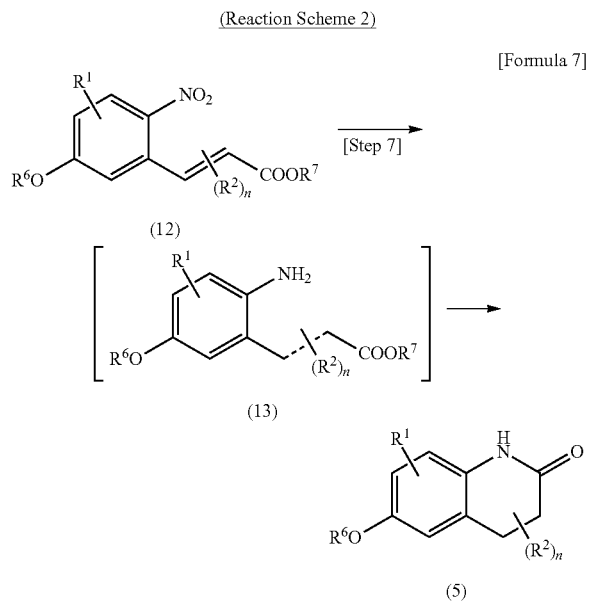

(Step 7)

Step 7 is intended to obtain compound (5) from compound (12). Compound (12) is known or may be easily synthesized from a known compound, for example, according to the method as described in Journal of Heterocyclic Chemistry, 1979, vol. 16, p. 221 or Synthesis, 1984, vol. 10, p. 862, or equivalent methods thereof. The reaction may be accomplished by reaction of compound (12) in a solvent under conditions used for reduction reaction, for example, according to the method described in Journal of American Chemical Society, 1944, vol. 66, p. 1442 or equivalent methods thereof. Conditions for reduction reaction available for use in this reaction include those for reaction in the presence of a catalyst (e.g., Raney Nickel or palladium on carbon) at normal or elevated pressure under a hydrogen atmosphere, those for reaction with a metal hydrogen complex compound (e.g., lithium aluminum hydride, sodium borohydride), those for reaction with iron(0), zinc(II) chloride or tin(II) chloride in the presence of an acid (e.g., acetic acid) or ammonium chloride, as well as combinations of these conditions. Examples of a solvent available for use in this reaction include alcohols (e.g., methanol, ethanol); ethers (e.g., tetrahydrofuran, 1,2-dimethoxyethane, 1,4-dioxane); hydrocarbons (e.g., toluene, benzene); halogenated hydrocarbons (e.g., chloroform, dichloromethane); amides (e.g., N,N-dimethylformamide, N,N-dimethylacetamide, N-methyl-2-pyrrolidone); ketones (e.g., acetone, 2-butanone); dimethyl sulfoxide; acetonitrile; or mixed solvents thereof. The reaction temperature in this reaction generally ranges from 0° C. to 200° C., preferably from 15° C. to 150° C., and the reaction time generally ranges from 1 to 48 hours, preferably from 1 to 16 hours.

Moreover, compound (13), which is a reaction intermediate in this step, may further be converted into compound (5) by intramolecular cyclization. The reaction may be accomplished by standard procedures for obtaining anilide through condensation between aniline and a carboxylic acid or ester, for example, through conversion of a carboxylic acid into a carboxylic acid halide (e.g., carboxylic acid chloride, carboxylic acid bromide) and the subsequent reaction with aniline, through conversion of a carboxylic acid into a mixed acid anhydride with chlorocarbonate ester or the like and the subsequent reaction with aniline, through conversion of a carboxylic acid into an active ester (e.g., 1-benzotriazolyl ester, succinimidyl ester) and the subsequent reaction with aniline, or through reaction in the presence of a dehydration condensing agent. All of these reactions may be accomplished in the presence or absence of an acid or a base with or without a solvent. Examples of a dehydration condensing agent available for use in this reaction include 3-(3-dimethylaminopropyl)-1-ethylcarbodiimide hydrochloride, dicyclohexylcarbodiimide, diphenylphosphorylazide, and carbonyldiimidazole. If necessary, it is possible to use an activator such as 1-hydroxybenzotriazole or hydroxysuccinimide. Examples of a base available for use in this reaction include pyridine, triethylamine, diisopropylethylamine, potassium carbonate, sodium carbonate, and sodium bicarbonate. Examples of a solvent available for use in this reaction include ethers (e.g., tetrahydrofuran, 1,2-dimethoxyethane, 1,4-dioxane); hydrocarbons (e.g., toluene, benzene); halogenated hydrocarbons (e.g., chloroform, dichloromethane); amides (e.g., N,N-dimethylformamide, N,N-dimethylacetamide, N-methyl-2-pyrrolidone); ketones (e.g., acetone, 2-butanone); dimethyl sulfoxide; acetonitrile; water; or mixed solvents thereof. The reaction temperature in this reaction generally ranges from 0° C. to 200° C., preferably from 15° C. to 150° C., and the reaction time generally ranges from 1 to 48 hours, preferably from 1 to 16 hours.

In a case where the dotted line in compound (13) is a double bond, the above intramolecular cyclization may be followed by reduction reaction for converting the double bond into a single bond to thereby obtain compound (5). The reaction may be accomplished by standard procedures for 1,4-reduction of an α,β-unsaturated ester or an α,β-unsaturated carboxylic acid, for example, through reaction under a hydrogen atmosphere using a transition metal catalyst (e.g., palladium on carbon, platinum oxide, Raney Nickel), through reaction in the presence of formic acid or triethylsilane using a transition metal catalyst, or through reaction in a protic solvent (e.g., alcohol) using a reducing agent (e.g., sodium borohydride). In this case, a transition metal chloride such as copper (II) chloride or nickel(II) chloride may be added, if necessary. Moreover, for example, an additive such as hydrochloric acid or acetic acid may be added, if necessary. These reactions may be performed in a solvent. Examples of a solvent available for use include alcohols (e.g., methanol, ethanol); ethers (e.g., tetrahydrofuran, 1,2-dimethoxyethane, 1,4-dioxane); hydrocarbons (e.g., toluene, benzene); halogenated hydrocarbons (e.g., chloroform, dichloromethane); amides (e.g., N,N-dimethylformamide, N,N-dimethylacetamide, N-methyl-2-pyrrolidone); ketones (e.g., acetone, 2-butanone); dimethyl sulfoxide; acetonitrile; water; or mixed solvents thereof. The reaction temperature in this reaction generally ranges from 0° C. to 200° C., preferably from 15° C. to 150° C., and the reaction time generally ranges from 1 to 48 hours, preferably from 1 to 16 hours.

Alternatively, compound (10) can also be prepared according to the process shown in Reaction Scheme 3.

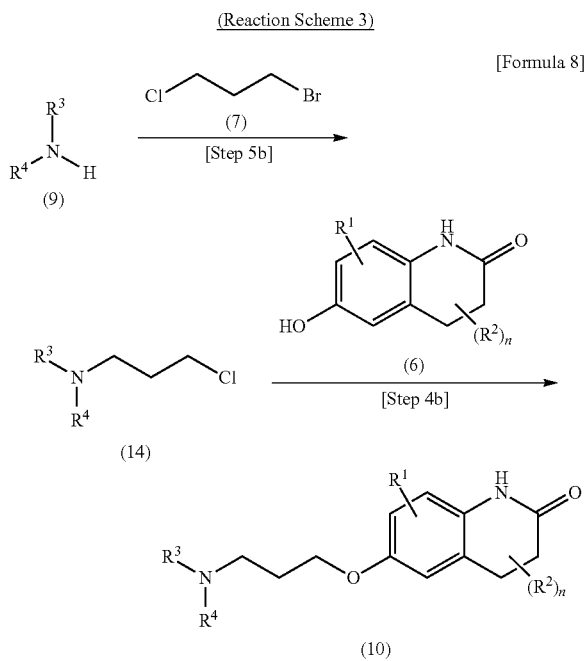

(Step 5b)
Step 5b is intended to obtain compound (14) by condensation between compounds (9) and (7) through coupling reaction. The reaction may be accomplished in the same manner as shown in Step 5a.

(Step 4b)
Step 4b is intended to obtain compound (10) by condensation between compounds (14) and (6) through coupling reaction. The reaction may be accomplished in the same manner as shown in Step 4a.

Explanation will be given below of the process shown in Reaction Scheme 4 for preparing the compound of the present invention. This process is intended to prepare the compound (1-3) of the present invention from compound (6).

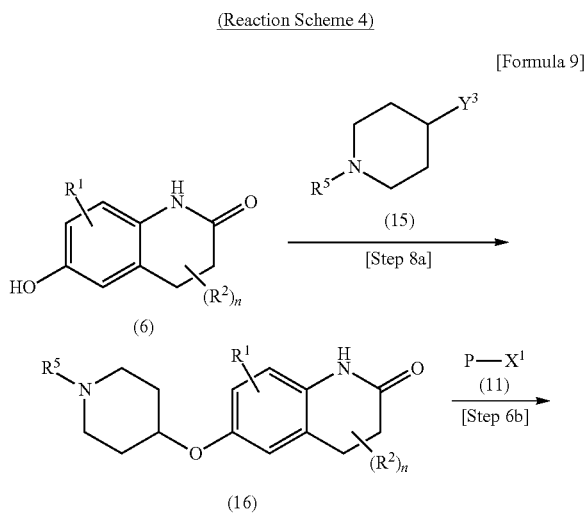

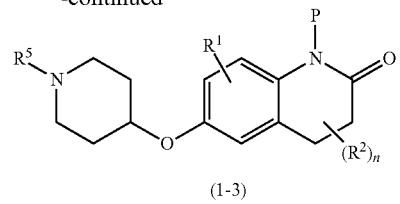

(Step 8a)
Step 8a is intended to obtain compound (16) by condensation between compounds (6) and (15) through coupling reaction. Compound (15) is known or may be easily synthesized from a known compound.

In a case where $Y^3$ is a leaving group such as a halogen atom or an organic sulfonyloxy group, the reaction may be accomplished by standard procedures for alkylation of the hydroxyl group in phenol in the presence or absence of a base with or without a solvent. If necessary, for example, an additive such as potassium iodide or sodium bromide may be added. Examples of a base available for use in this reaction include organic bases such as pyridine, triethylamine, and diisopropylethylamine; as well as inorganic bases such as potassium tert-butoxide, potassium carbonate, cesium carbonate, sodium bicarbonate, sodium hydroxide, potassium hydroxide, and sodium hydride. Examples of a solvent available for use in this reaction include alcohols (e.g., methanol, ethanol, isopropanol); ethers (e.g., tetrahydrofuran, 1,2-dimethoxyethane, 1,4-dioxane); hydrocarbons (e.g., toluene, benzene); halogenated hydrocarbons (e.g., chloroform, dichloromethane); amides (e.g., N,N-dimethylformamide, N,N-dimethylacetamide, N-methyl-2-pyrrolidone); ketones (e.g., acetone, 2-butanone); dimethyl sulfoxide; acetonitrile; water; or mixed solvents thereof. The reaction temperature in this reaction generally ranges from 0° C. to 200° C., preferably from 15° C. to 150° C., and the reaction time generally ranges from 1 to 48 hours, preferably from 1 to 16 hours.

In a case where $Y^3$ is a hydroxyl group, the reaction may be Mitsunobu reaction, for example, which is accomplished in a solvent in the presence of a reagent composed of an organophosphorus compound (e.g., triphenylphosphine, tributylphosphine) in combination with an azo compound (e.g., diethyl azodicarboxylate, diisopropyl azodicarboxylate, di-tert-butyl azodicarboxylate) or in the presence of a phosphorus glide reagent (e.g., cyanomethyltributylphosphorane). Examples of a solvent available for use in this reaction include ethers (e.g., tetrahydrofuran, 1,2-dimethoxyethane, 1,4-dioxane); hydrocarbons (e.g., toluene, benzene); halogenated hydrocarbons (e.g., chloroform, dichloromethane); amides (e.g., N,N-dimethylformamide, N,N-dimethylacetamide, N-methyl-2-pyrrolidone); ketones (e.g., acetone, 2-butanone); dimethyl sulfoxide; acetonitrile; or mixed solvents thereof. The reaction temperature in this reaction generally ranges from 0° C. to 150° C., preferably from 15° C. to 100° C., and the reaction time generally ranges from 1 to 48 hours, preferably from 1 to 16 hours.

(Step 6b)
Step 6b is intended to obtain the compound (1-3) of the present invention by condensation between compounds (16) and (11) through cross-coupling reaction. The reaction may be accomplished in the same manner as shown in Step 6a.

Explanation will be given below of the process shown in Reaction Scheme 5 for preparing the compound of the present invention. This process is intended to prepare the compound (1-3) of the present invention from compound (6).

(Reaction Scheme 5)

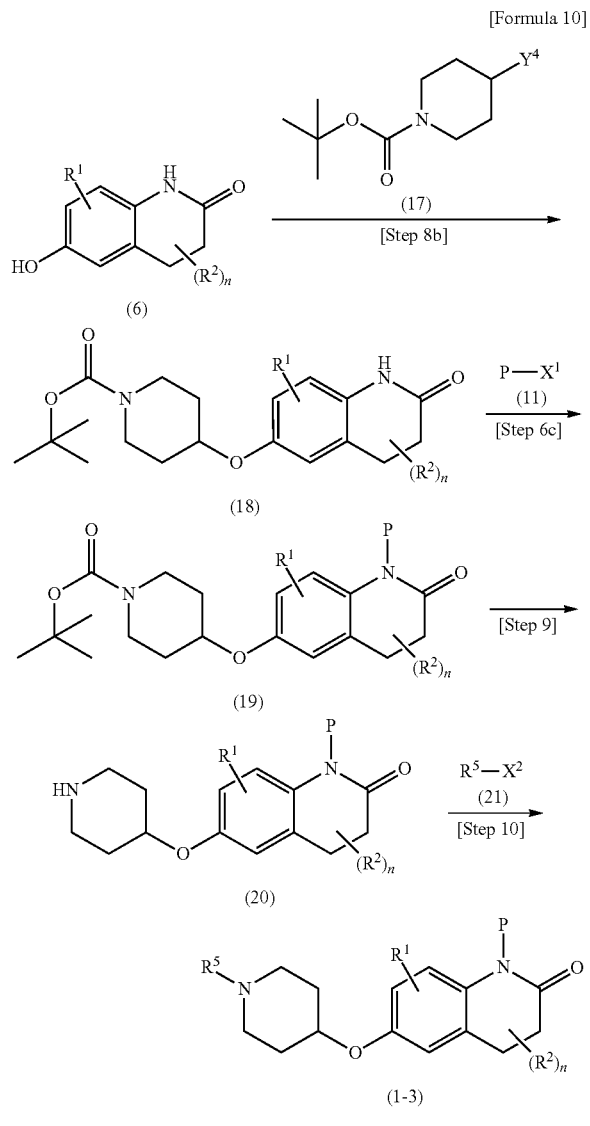

reaction include hydrochloric acid, sulfuric acid, trifluoroacetic acid, and trifluoromethanesulfonic acid. Examples of a base available for use in this reaction include sodium hydroxide, and potassium hydroxide. Examples of a solvent available for use in this reaction include alcohols (e.g., methanol, ethanol, isopropanol); ethers (e.g., tetrahydrofuran, 1,4-dioxane); hydrocarbons (e.g., toluene, benzene); halogenated hydrocarbons (e.g., chloroform, dichloromethane); amides (e.g., N,N-dimethylformamide, N,N-dimethylacetamide, N-methyl-2-pyrrolidone); ketones (e.g., acetone, 2-butanone); dimethyl sulfoxide; acetonitrile; water; or mixed solvents thereof. The reaction temperature in this reaction generally ranges from 0° C. to 150° C., preferably from 15° C. to 40° C., and the reaction time generally ranges from 1 to 48 hours, preferably from 1 to 12 hours.

(Step 10)

Step 10 is intended to obtain the compound (1-3) of the present invention by condensation between compounds (20) and (21) through coupling reaction. Compound (21) is known or may be easily synthesized from a known compound. The reaction may be accomplished in the same manner as shown in Step 5a.

Alternatively, the compound (1-3) of the present invention can also be prepared according to the process shown in Reaction Scheme 6.

(Reaction Scheme 6)

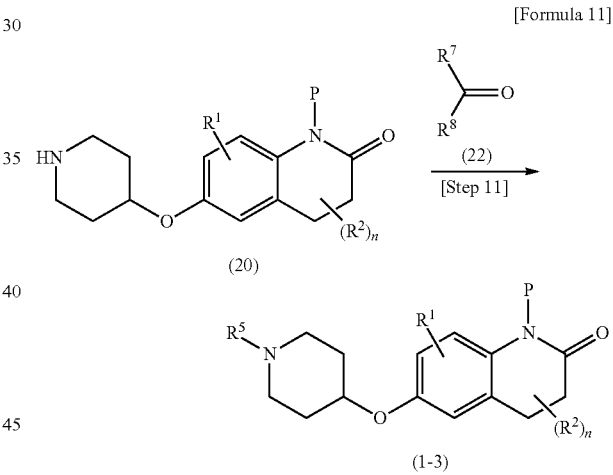

(Step 8b)

Step 8b is intended to obtain compound (18) by condensation between compounds (6) and (17) through coupling reaction. Compound (17) is known or may be easily synthesized from a known compound. The reaction may be accomplished in the same manner as shown in Step 8a.

(Step 6c)

Step 6c is intended to obtain compound (19) by condensation between compounds (18) and (11) through coupling reaction. The reaction may be accomplished in the same manner as shown in Step 6a.

(Step 9)

Step 9 is intended to obtain compound (20) by removal of the tert-butoxycarbonyl group in compound (19). The reaction may be accomplished by standard procedures for deprotection of tert-butoxycarbonyl groups, for example, in the presence of a strong acid with or without a solvent, or alternatively, in the presence of a base in a solvent, according to the method described in T. W. Greene and P. G. M. Wuts, Protective Groups in Organic Synthesis or equivalent methods thereof. Examples of an acid available for use in this (Step 11)

Step 11 is intended to obtain the compound (1-3) of the present invention by condensation between compounds (20) and (22) through reductive condensation reaction. The reaction may be accomplished by standard procedures for reductive amination through condensation between a carbonyl compound and an amine, for example, by adding a reducing agent to a mixture of compounds (20) and (22) in the presence or absence of an acid with or without a solvent. As another example, it is possible to use catalytic reduction through hydrogenation using a catalyst such as palladium on carbon, platinum, Raney Nickel or rhodium-alumina. Examples of a reducing agent available for use in this reaction include sodium borohydride, sodium triacetoxyborohydride, sodium cyanoborohydride, diborane, and lithium aluminum hydride. Examples of an acid available for use in this reaction include organic acids (e.g., acetic acid, formic acid); inorganic acids (e.g., hydrochloric acid, sulfuric acid); as well as Lewis acids (e.g., titanium chloride, zinc chloride, ytterbium(III) triflate).

Examples of a solvent available for use in this reaction include alcohols (e.g., methanol, ethanol, isopropanol); ethers (e.g., tetrahydrofuran, 1,4-dioxane); hydrocarbons (e.g., toluene, benzene); halogenated hydrocarbons (e.g., chloroform, dichloromethane); acetonitrile; water; or mixed solvents thereof. The reaction temperature in this reaction generally ranges from 0° C. to 150° C., preferably from 15° C. to 40° C., and the reaction time generally ranges from 1 to 48 hours, preferably from 1 to 12 hours.

The present invention will be further described in more detail by way of the following examples and test examples, which are not intended to limit the scope of the invention.

EXAMPLES

Example 1

Preparation of 4-[6-{3-[(2R)-2-methylpyrrolidin-1-yl]propoxy}-2-oxo-3,4-dihydroquinolin-1(2H)-yl]benzonitrile (Compound No. 1)

(1) Preparation of (2R)-1-(3-chloropropyl)-2-methylpyrrolidine

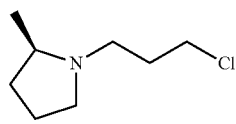

[Chemical 12]

To a solution of (R)-2-methylpyrrolidine (18.0 g) and 1-bromo-3-chloropropane (100.0 g) in acetone (360 mL), 5M aqueous sodium hydroxide (50 mL) was added dropwise in an ice bath and stirred at 80° C. for 4 hours. The reaction mixture was cooled to room temperature and extracted with diethyl ether. The organic layer was washed with brine, dried over anhydrous sodium sulfate and concentrated under reduced pressure, and the resulting residue was purified by NH-type silica gel column chromatography (eluting solvent: n-hexane/ethyl acetate=4/1 to 1/1) and silica gel column chromatography (eluting solvent: chloroform/methanol=9/1) to give the titled compound (17.8 g, 52%) as a yellow oil.

(2) Preparation of (2R)-6-[3-(2-methylpyrrolidin-1-yl)propoxy]-3,4-dihydroquinolin-2(1H)-one

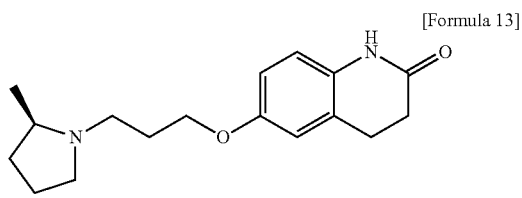 [SMILES: C[C@@H]1CCCN1CCCOc1ccc2c(c1)CCC(=O)N2]

[Formula 13]

To a solution of 6-hydroxy-3,4-dihydroquinolin-2(1H)-one (0.55 g) in acetonitrile (10 mL), cesium carbonate (2.0 g) and (2R)-1-(3-chloropropyl)-2-methylpyrrolidine prepared in Example 1-(1) (0.50 g) were added and stirred at 100° C. for 1 hour. The reaction mixture was diluted with water and extracted with ethyl acetate. The organic layer was dried over anhydrous magnesium sulfate and concentrated under reduced pressure, and the resulting residue was purified by NH-type silica gel column chromatography (eluting solvent: n-hexane/ethyl acetate=1/1). The resulting solid was subjected to recrystallization from n-hexane to give the titled compound (0.33 g, 37%) as a colorless powder.

(3) Preparation of 4-[6-{3-[(2R)-2-methylpyrrolidin-1-yl]propoxy}-2-oxo-3,4-dihydroquinolin-1(2H)-yl]benzonitrile (Compound No. 1)

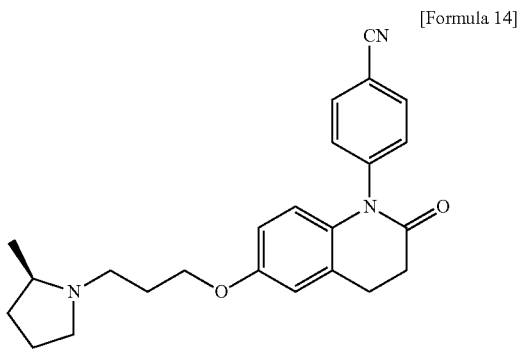 [SMILES: C[C@@H]1CCCN1CCCOc1ccc2c(c1)CCC(=O)N2c1ccc(C#N)cc1]

[Formula 14]

A suspension of (2R)-6-[3-(2-methylpyrrolidin-1-yl)propoxy]-3,4-dihydroquinolin-2(1H)-one prepared in Example 1-(2) (0.20 g), 4-iodobenzonitrile (0.18 g), rac-trans-N,N'-dimethylcyclohexane-1,2-diamine (0.041 g), copper iodide (0.013 g) and cesium carbonate (0.45 g) in N,N-dimethylformamide (2 mL) was stirred at 100° C. for 16 hours. The reaction mixture was diluted with water and extracted with chloroform. The organic layer was dried over anhydrous sodium sulfate and concentrated under reduced pressure. The resulting residue was purified by preparative TLC (on a single plate of 2 mm thickness, developing solvent: chloroform/methanol=9/1) and NH-type preparative TLC (on two plates of 0.25 mm thickness, developing solvent: n-hexane/ethyl acetate=1/1) to give the titled compound (0.062 g, 23%) as a light-brown amorphous substance.

$^1$H NMR (600 MHz, CHLOROFORM-d) δ ppm 1.07 (d, J=6.0 Hz, 3 H), 1.36-1.45 (m, 1 H), 1.63-2.34 (m, 8 H), 2.75-2.85 (m, 2 H), 2.91-3.05 (m, 3 H), 3.11-3.20 (m, 1 H), 3.93-4.01 (m, 2 H), 6.24 (d, J=8.7 Hz, 1 H), 6.59 (dd, J=8.7, 2.8 Hz, 1 H), 6.78 (d, J=3.2 Hz, 1 H), 7.38 (d, J=8.7 Hz, 2 H), 7.76 (d, J=8.7 Hz, 2 H)

MS (ESI/APCI Dual) (Positive) m/z; 390(M+H)$^+$

The same procedure as shown in Example 1 was repeated to prepare the compounds listed below:

6-{3-[(2R)-2-methylpyrrolidin-1-yl]propoxy}-1-phenyl-3,4-dihydroquinolin-2(1H)-one (Compound No. 2);

1-(4-methylphenyl)-6-{3-[(2R)-2-methylpyrrolidin-1-yl]propoxy}-3,4-dihydroquinolin-2(1H)-one (Compound No. 3);

1-(4-methoxyphenyl)-6-{3-[(2R)-2-methylpyrrolidin-1-yl]propoxy}-3,4-dihydroquinolin-2(1H)-one (Compound No. 4);

1-(4-ethoxyphenyl)-6-{3-[(2R)-2-methylpyrrolidin-1-yl]propoxy}-3,4-dihydroquinolin-2(1H)-one (Compound No. 5);

1-(4-fluorophenyl)-6-{3-[(2R)-2-methylpyrrolidin-1-yl]propoxy}-3,4-dihydroquinolin-2(1H)-one (Compound No. 6);

1-(4-chlorophenyl)-6-{3-[(2R)-2-methylpyrrolidin-1-yl]propoxy}-3,4-dihydroquinolin-2(1H)-one (Compound No. 7);

6-{3-[(2R)-2-methylpyrrolidin-1-yl]propoxy}-1-[4-(trifluoromethyl)phenyl]-3,4-dihydroquinolin-2(1H)-one (Compound No. 8);

6-{3-[(2R)-2-methylpyrrolidin-1-yl]propoxy}-1-[4-(trifluoromethoxy)phenyl]-3,4-dihydroquinolin-2(1H)-one (Compound No. 9);

1-[4-(hydroxymethyl)phenyl]-6-{3-[(2R)-2-methylpyrrolidin-1-yl]propoxy}-3,4-dihydroquinolin-2(1H)-one (Compound No. 10);

1-[4-(methoxymethyl)phenyl]-6-{3-[(2R)-2-methylpyrrolidin-1-yl]propoxy}-3,4-dihydroquinolin-2(1H)-one (Compound No. 11);

1-{4-[(dimethylamino)methyl]phenyl}-6-{3-[(2R)-2-methylpyrrolidin-1-yl]propoxy}-3,4-dihydroquinolin-2(1H)-one (Compound No. 12);

N,N-dimethyl-4-[6-{3-[(2R)-2-methylpyrrolidin-1-yl]propoxy}-2-oxo-3,4-dihydroquinolin-1(2H)-yl]benzamide (Compound No. 13);

6-{3-[(2R)-2-methylpyrrolidin-1-yl]propoxy}-1-[4-(pyrrolidin-1-ylcarbonyl)phenyl]-3,4-dihydroquinolin-2(1H)-one (Compound No. 14);

1-(4-acetylphenyl)-6-{3-[(2R)-2-methylpyrrolidin-1-yl]propoxy}-3,4-dihydroquinolin-2(1H)-one (Compound No. 15);

1-[4-(cyclopropylcarbonyl)phenyl]-6-{3-[(2R)-2-methylpyrrolidin-1-yl]propoxy}-3,4-dihydroquinolin-2(1H)-one (Compound No. 16);

6-{3-[(2R)-2-methylpyrrolidin-1-yl]propoxy}-1-[4-(morpholin-4-yl)phenyl]-3,4-dihydroquinolin-2(1H)-one (Compound No. 17);

6-{3-[(2R)-2-methylpyrrolidin-1-yl]propoxy}-1-[4-(2-oxopyrrolidin-1-yl)phenyl]-3,4-dihydroquinolin-2(1H)-one (Compound No. 18);

6-{3-[(2R)-2-methylpyrrolidin-1-yl]propoxy}-1-[4-(1,3-oxazol-5-yl)phenyl]-3,4-dihydroquinolin-2(1H)-one (Compound No. 19);

1-{4-[(6-methylpyridazin-3-yl)oxy]phenyl}-6-{3-[(2R)-2-methylpyrrolidin-1-yl]propoxy}-3,4-dihydroquinolin-2(1H)-one (Compound No. 20);

N,N-dimethyl-3-[6-{3-[(2R)-2-methylpyrrolidin-1-yl]propoxy}-2-oxo-3,4-dihydroquinolin-1(2H)-yl]benzamide (Compound No. 21);

1-(3-methoxyphenyl)-6-{3-[(2R)-2-methylpyrrolidin-1-yl]propoxy}-3,4-dihydroquinolin-2(1H)-one (Compound No. 22);

1-(2-methoxyphenyl)-6-{3-[(2R)-2-methylpyrrolidin-1-yl]propoxy}-3,4-dihydroquinolin-2(1H)-one (Compound No. 23);

1-(3-fluorophenyl)-6-{3-[(2R)-2-methylpyrrolidin-1-yl]propoxy}-3,4-dihydroquinolin-2(1H)-one (Compound No. 24);

1-(2,4-dimethoxyphenyl)-6-{3-[(2R)-2-methylpyrrolidin-1-yl]propoxy}-3,4-dihydroquinolin-2(1H)-one (Compound No. 25);

1-(3-fluoro-5-methoxyphenyl)-6-{3-[(2R)-2-methylpyrrolidin-1-yl]propoxy}-3,4-dihydroquinolin-2(1H)-one (Compound No. 26);

1-(3,5-difluorophenyl)-6-{3-[(2R)-2-methylpyrrolidin-1-yl]propoxy}-3,4-dihydroquinolin-2(1H)-one (Compound No. 27);

1-(3,4-difluorophenyl)-6-{3-[(2R)-2-methylpyrrolidin-1-yl]propoxy}-3,4-dihydroquinolin-2(1H)-one (Compound No. 28);

1-(2,4-difluorophenyl)-6-{3-[(2R)-2-methylpyrrolidin-1-yl]propoxy}-3,4-dihydroquinolin-2(1H)-one (Compound No. 29);

1-(4-chloro-2-fluorophenyl)-6-{3-[(2R)-2-methylpyrrolidin-1-yl]propoxy}-3,4-dihydroquinolin-2(1H)-one (Compound No. 30);

3-chloro-5-[6-{3-[(2R)-2-methylpyrrolidin-1-yl]propoxy}-2-oxo-3,4-dihydroquinolin-1(2H)-yl]benzonitrile (Compound No. 31);

2-methyl-5-[6-{3-[(2R)-2-methylpyrrolidin-1-yl]propoxy}-2-oxo-3,4-dihydroquinolin-1(2H)-yl]benzonitrile (Compound No. 32);

2-methoxy-5-[6-{3-[(2R)-2-methylpyrrolidin-1-yl]propoxy}-2-oxo-3,4-dihydroquinolin-1(2H)-yl]benzonitrile (Compound No. 33);

6-{3-[(2R)-2-methylpyrrolidin-1-yl]propoxy}-1-(pyridin-2-yl)-3,4-dihydroquinolin-2(1H)-one (Compound No. 34);

6-{3-[(2R)-2-methylpyrrolidin-1-yl]propoxy}-1-(pyridin-3-yl)-3,4-dihydroquinolin-2(1H)-one (Compound No. 35);

6-{3-[(2R)-2-methylpyrrolidin-1-yl]propoxy}-1-(pyrimidin-5-yl)-3,4-dihydroquinolin-2(1H)-one (Compound No. 36);

6-{3-[(2R)-2-methylpyrrolidin-1-yl]propoxy}-3,4-dihydro-2H-1,3'-biquinolin-2-one (Compound No. 37);

6-{3-[(2R)-2-methylpyrrolidin-1-yl]propoxy}-3,4-dihydro-2H-1,6'-biquinolin-2-one (Compound No. 38);

6-{3-[(2R)-2-methylpyrrolidin-1-yl]propoxy}-1-(1,5-naphthylizin-3-yl)-3,4-dihydroquinolin-2(1H)-one (Compound No. 39);

6-{3-[(2R)-2-methylpyrrolidin-1-yl]propoxy}-1-(1,6-naphthylizin-8-yl)-3,4-dihydroquinolin-2(1H)-one (Compound No. 40);

tert-butyl 5-[6-{3-[(2R)-2-methylpyrrolidin-1-yl]propoxy}-2-oxo-3,4-dihydroquinolin-1(2H)-yl]-1H-indole-1-carboxylate (Compound No. 41);

tert-butyl 3-[6-{3-[(2R)-2-methylpyrrolidin-1-yl]propoxy}-2-oxo-3,4-dihydroquinolin-1(2H)-yl]-1H-indole-1-carboxylate (Compound No. 42);

1-(2,3-dihydro-1,4-benzodioxin-6-yl)-6-{3-[(2R)-2-methylpyrrolidin-1-yl]propoxy}-3,4-dihydroquinolin-2(1H)-one (Compound No. 43);

1-(1,3-benzodioxol-5-yl)-6-{3-[(2R)-2-methylpyrrolidin-1-yl]propoxy}-3,4-dihydroquinolin-2(1H)-one (Compound No. 44);

1-(2,3-dihydro-1-benzofuran-6-yl)-6-{3-[(2R)-2-methylpyrrolidin-1-yl]propoxy}-3,4-dihydroquinolin-2(1H)-one (Compound No. 45);

6-[6-{3-[(2R)-2-methylpyrrolidin-1-yl]propoxy}-2-oxo-3,4-dihydroquinolin-1(2H)-yl]pyridine-3-carbonitrile (Compound No. 46);

1-(6-methylpyridin-3-yl)-6-{3-[(2R)-2-methylpyrrolidin-1-yl]propoxy}-3,4-dihydroquinolin-2(1H)-one (Compound No. 47);

1-(6-methoxypyridin-3-yl)-6-{3-[(2R)-2-methylpyrrolidin-1-yl]propoxy}-3,4-dihydroquinolin-2(1H)-one (Compound No. 48);

1-(5-chloropyridin-2-yl)-6-{3-[(2R)-2-methylpyrrolidin-1-yl]propoxy}-3,4-dihydroquinolin-2(1H)-one (Compound No. 49);

5-[6-{3-[(2R)-2-methylpyrrolidin-1-yl]propoxy}-2-oxo-3,4-dihydroquinolin-1(2H)-yl]pyridine-3-carbonitrile (Compound No. 50);

2-[6-{3-[(2R)-2-methylpyrrolidin-1-yl]propoxy}-2-oxo-3,4-dihydroquinolin-1(2H)-yl]pyridine-3-carbonitrile (Compound No. 51);

1-(5-fluoropyridin-3-yl)-6-{3-[(2R)-2-methylpyrrolidin-1-yl]propoxy}-3,4-dihydroquinolin-2(1H)-one (Compound No. 52);

1-(3-methylpyridin-2-yl)-6-{3-[(2R)-2-methylpyrrolidin-1-yl]propoxy}-3,4-dihydroquinolin-2(1H)-one (Compound No. 53);
1-(1-methyl-2-oxo-1,2-dihydropyridin-4-yl)-6-{3-[(2R)-2-methylpyrrolidin-1-yl]propoxy}-3,4-dihydroquinolin-2(1H)-one (Compound No. 54); and 6'-methoxy-6-{3-[(2R)-2-methylpyrrolidin-1-yl]propoxy}-3,4-dihydro-2H-1,3'-biquinolin-2-one (Compound No. 55).

The structural formulae as well as physical and chemical data of Compound Nos. 2 to 55 are shown in Table 1.

TABLE 1

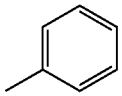

| Compound No. | P | MS (ESI/APCI) MH⁺ | ¹H NMR |
|---|---|---|---|
| 2 | 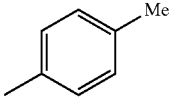 | 365 | (600 MHz, CHLOROFORM-d) δ ppm 1.12 (d, J = 5.0 Hz, 3 H), 1.41-2.45 (m, 9 H), 2.76-2.84 (m, 2 H), 2.95-3.07 (m, 3 H), 3.15-3.27 (m, 1 H), 3.93-4.02 (m, 2 H), 6.26 (d, J = 8.7 Hz, 1 H), 6.57 (dd, J = 8.7, 2.8 Hz, 1 H) 6.77 (d, J = 2.8 Hz, 1 H), 7.20-7.25 (m, 2 H), 7.37-7.42 (m, 1 H), 7.46-7.52 (m, 2 H) |
| 3 | 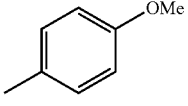 | 379 | (600 MHz, CHLOROFORM-d) δ ppm 1.06-1.18 (m, 3 H), 1.38-2.38 (m, 9 H), 2.41 (s, 3 H), 2.76-2.83 (m, 2 H), 2.93-3.05 (m, 3 H), 3.15-3.27 (m, 1 H), 3.93-4.03 (m, 2 H), 6.29 (d, J = 8.7 Hz, 1 H), 6.56 (dd, J = 8.7, 2.8 Hz, 1 H), 6.76 (d, J = 2.8 Hz, 1 H), 7.08-7.13 (m, 2 H), 7.28-7.32 (m, 2 H) |
| 4 | 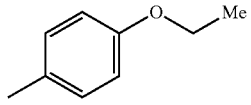 | 395 | (600 MHz, CHLOROFORM-d) δ ppm 1.09 (d, J = 6.0 Hz, 3 H), 1.37-1.46 (m, 1 H), 1.65-1.82 (m, 2 H), 1.86-2.21 (m, 5 H), 2.24-2.34 (m, 1 H), 2.76-2.81 (m, 2 H), 2.92-3.03 (m, 3 H), 3.14-3.19 (m, 1 H), 3.85 (s, 3 H) 3.94-4.01 (m, 2 H), 6.30 (d, J = 8.7 Hz, 1 H), 6.58 (dd, J = 8.9, 3.0 Hz, 1 H), 6.76 (d, J = 2.8 Hz, 1 H), 6.98-7.03 (m, 2 H), 7.11-7.16 (m, 2 H) |
| 5 | 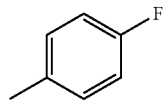 | 409 | (600 MHz, CHLOROFORM-d) δ ppm 1.15 (d, J = 6.0 Hz, 3 H), 1.44 (t, J = 6.9 Hz, 3 H), 1.47-2.52 (m, 9 H), 2.76-2.83 (m, 2 H), 2.97-3.05 (m, 3 H), 3.20-3.29 (m 1 H), 3.93-4.02 (m, 2 H) 4.07 (q, J = 6.9 Hz, 2 H) 6.30 (d, J = 8.7 Hz, 1 H), 6.57 (dd, J = 8.7, 2.8 Hz, 1 H), 6.76 (d, J = 2.8 Hz, 1 H), 6.94-7.03 (m, 2 H), 7.09-7.15 (m, 2 H) |
| 6 | 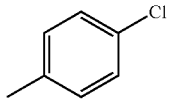 | 383 | (600 MHz, CHLOROFORM-d) δ ppm 1.02-1.19 (m, 3 H), 1.37-2.43 (m, 9 H), 2.77-2.82 (m, 2 H), 2.92-3.05 (m, 3 H), 3.14-3.24 (m, 1 H), 3.95-4.02 (m, 2 H), 6.26 (d, J = 8.9 Hz, 1 H), 6.59 (dd, J = 8.9, 2.8 Hz, 1 H), 6.78 (d, J = 2.8 Hz, 1 H), 7.15-7.23 (m, 4 H) |
| 7 |  | 399 | (600 MHz, CHLOROFORM-d) δ ppm 1.09 (d, J = 5.5 Hz, 3 H), 1.42 (br. s., 1 H), 1.65-1.83 (m, 2 H), 1.85-2.02 (m, 3 H), 2.04-2.35 (m, 3 H), 2.79 (dd, J = 8.5, 6.2 Hz, 2 H), 2.91-3.05 (m, 3 H), 3.17 (br. s., 1 H), 3.93-4.02 (m, 2 H), 6.27 (d, J = 8.7 Hz, 1 H), 6.59 (dd, J = 9.2, 2.8 Hz, 1 H), 6.78 (d, J = 2.8 Hz, 1 H), 7.14-7.20 (m, 2 H), 7.42-7.48 (m, 2 H) |
| 8 | 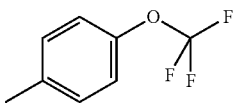 | 433 | (600 MHz, CHLOROFORM-d) δ ppm 1.07 (d, J = 6.0 Hz, 3 H), 1.36-1.44 (m, 1 H), 1.65-1.71 (m, 1 H), 1.72-1.81 (m, 1 H), 1.87-1.99 (m, 3 H), 2.06-2.12 (m, 1 H), 2.14-2.19 (m, 1 H), 2.24-2.31 (m, 1 H), 2.77-2.82 (m, 2 H), 2.91-2.97 (m, 1 H), 3.00-3.04 (m, 2 H), 3.15 (td, J = 8.6, 2.5 Hz, 1 H), 3.90-4.02 (m, 2 H), 6.24 (d, J = 8.7 Hz, 1 H), 6.58 (dd, J = 8.7, 2.8 Hz, 1 H), 6.79 (d, J = 2.8 Hz, 1 H), 7.37 (d, J = 8.3 Hz, 2 H), 7.74 (d, J = 8.3 Hz, 2 H) |
| 9 | 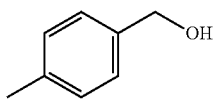 | 449 | (600 MHz, CHLOROFORM-d) δ ppm 1.03-1.17 (m, 3 H), 1.39-2.52 (m, 9 H), 2.76-2.83 (m, 2 H), 2.93-3.05 (m, 3 H), 3.15-3.27 (m, 1 H), 3.94-4.04 (m, 2 H), 6.26 (d, J = 8.7 Hz, 1 H), 6.60 (dd, J = 8.7, 2.8 Hz, 1 H), 6.78 (d, J = 2.8 Hz, 1 H), 7.24-7.29 (m, 2 H), 7.30-7.36 (m, 2 H) |
| 10 |  | 395 | (600 MHz, CHLOROFORM-d) δ ppm 1.13 (d, J = 6.0 Hz, 3 H), 1.48-2.69 (m, 9 H), 2.75-2.85 (m, 2 H), 2.96-3.14 (m, 3 H), 3.24-3.44 (m, 1 H), 3.95-4.03 (m, 2 H), 4.76 (s, 2 H), 6.28 (d, J = 8.7 Hz, 1 H), 6.56 (dd, J = 8.7, 2.8 Hz, 1 H), 6.77 (d, J = 2.8 Hz, 1 H), 7.20-724 (m, 2 H), 7.47-7.53 (m, 2 H) |

TABLE 1-continued

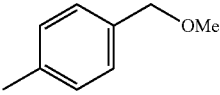

| Compound No. | P | MS (ESI/APCI) MH+ | ¹H NMR |
|---|---|---|---|
| 11 | 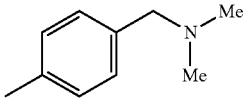 | 409 | (600 MHz, CHLOROFORM-d) δ ppm 1.07-1.16 (m, 3 H), 1.33-2.48 (m, 9 H), 2.77-2.82 (m, 2 H), 2.92-3.05 (m, 3 H), 3.14-3.25 (m, 1 H), 3.45 (s, 3 H), 3.94-4.01 (m, 2 H), 4.51 (s, 2 H), 6.27 (d, J = 9.2 Hz, 1 H), 6.55 (dd, J = 9.2, 2.8 Hz, 1 H), 6.77 (d, J = 2.8 Hz, 1 H), 7.20-7.23 (m, 2 H), 7.45-7.48 (m, 2 H) |
| 12 | 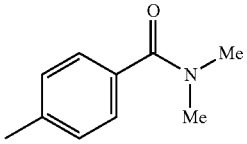 | 422 | (600 MHz, CHLOROFORM-d) δ ppm 1.10 (d, J = 5.5 Hz, 3 H), 1.33-2.25 (m, 9 H), 2.29 (s, 6 H), 2.77-2.82 (m, 2 H), 2.93-3.04 (m, 3 H), 3.13-3.24 (m, 1 H), 3.47 (s, 2 H), 3.92-4.04 (m, 2 H), 6.27 (d, J = 9.2 Hz, 1 H), 6.56 (dd, J = 9.2, 2.8 Hz, 1 H), 6.77 (d, J = 2.8 Hz, 1 H), 7.16-7.20 (m, 2 H), 7.41-7.45 (m, 2 H) |
| 13 | 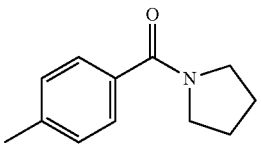 | 436 | (600 MHz, CHLOROFORM-d) δ ppm 1.09 (d, J = 6.4 Hz, 3 H), 1.36-1.47 (m, 1 H), 1.59-1.84 (m, 2 H), 1.87-2.03 (m, 3 H), 2.04-2.22 (m, 2 H), 2.23-2.34 (m, 1 H), 2.76-2.83 (m, 2 H), 2.91-3.22 (m, 10 H), 3.93-4.02 (m, 2 H), 6.29 (d, J = 8.7 Hz, 1 H), 6.57 (dd, J = 8.7, 2.8 Hz, 1 H), 6.78 (d, J = 2.8 Hz, 1 H), 7.29 (d, J = 8.3 Hz, 2 H), 7.55 (d, J = 8.3 Hz, 2 H) |
| 14 | 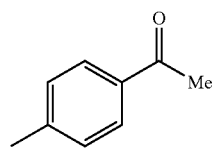 | 462 | (600 MHz, CHLOROFORM-d) δ ppm 1.13 (d, J = 6.0 Hz, 3 H), 1.41-1.53 (m, 1 H), 1.55-2.46 (m, 12 H), 2.73-2.84 (m, 2 H), 2.93-3.05 (m, 3 H), 3.16-3.27 (m 1 H), 3.51 (t, J = 6.6 Hz, 2 H), 3.61-3.70 (m 2 H), 3.92-4.03 (m, 2 H), 6.28 (d, J = 8.7 Hz, 1 H), 6.57 (dd, J = 8.7, 2.8 Hz, 1 H), 6.77 (d, J = 3.2 Hz, 1 H), 7.28 (d, J = 8.3 Hz, 2 H), 7.64 (d, J = 8.3 Hz, 2 H) |
| 15 | 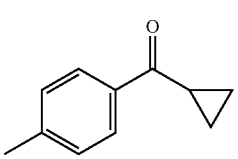 | 407 | (600 MHz, CHLOROFORM-d) δ ppm 1.08 (d, J = 6.0 Hz, 3 H), 1.37-1.45 (m, 1 H), 1.65-1.81 (m, 2 H), 1.88-2.01 (m, 3 H), 2.07-2.13 (m, 1 H), 2.15-2.20 (m, 1 H), 2.25-2.32 (m, 1 H), 2.64 (s, 3 H), 2.79-2.83 (m, 2 H), 2.92-2.99 (m, 1 H), 3.01-3.05 (m, 2 H), 3.14-3.18 (m, 1 H), 3.94-4.02 (m, 2 H), 6.27 (d, J = 8.9 Hz, 1 H), 6.58 (dd, J = 8.9, 2.8 Hz, 1 H), 6.79 (d, J = 2.8 Hz, 1 H), 7.34-7.38 (m, 2 H), 8.04-8.11 (m, 2 H) |
| 16 | 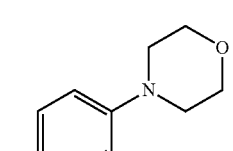 | 433 | (600 MHz, CHLOROFORM-d) δ ppm 0.88-1.48 (m, 8 H), 1.52-2.37 (m, 9 H), 2.77-2.83 (m, 2 H), 2.91-3.08 (m, 3 H), 3.10-3.27 (m, 1 H), 3.90-4.07 (m, 2 H), 6.28 (d, J = 8.7 Hz, 1 H), 6.58 (dd, J = 8.7, 2.8 Hz, 1 H), 6.79 (d, J = 2.8 Hz, 1 H), 7.37 (d, J = 8.7 Hz, 2 H), 8.13 (d, J = 8.3 Hz, 2 H) |
| 17 | 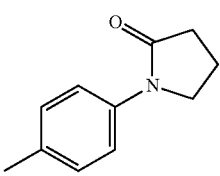 | 450 | (600 MHz, CHLOROFORM-d) δ ppm 1.08 (d, J = 6.0 Hz, 3 H), 1.36-1.46 (m, 1 H), 1.63-1.82 (m, 2 H), 1.87-2.01 (m, 3 H), 2.05-2.12 (m, 1 H), 2.13-2.20 (m, 1 H), 2.23-2.31 (m, 1 H), 2.75-2.82 (m, 2 H), 2.91-3.04 (m, 3 H), 3.13-3.18 (m, 1 H), 3.19-3.25 (m, 4 H), 3.83-3.90 (m, 4 H), 3.92-4.01 (m, 2 H), 6.32 (d, J = 8.7 Hz, 1 H), 6.57 (dd, J = 8.9, 3.0 Hz, 1 H), 6.76 (d, J = 2.8 Hz, 1 H), 6.97-7.02 (m, 2 H), 7.09-7.13 (m, 2 H) |
| 18 |  | 448 | (600 MHz, CHLOROFORM-d) δ ppm 1.08 (d, J = 6.0 Hz, 3 H), 1.35-1.48 (m, 1 H), 1.58-1.82 (m, 2 H), 1.85-2.03 (m, 3 H), 2.05-2.34 (m, 5 H), 2.65 (t, J = 8.0 Hz, 2 H), 2.74-2.86 (m, 2 H), 2.90-3.07 (m, 3 H), 3.12-3.21 (m, 1 H), 3.86-4.03 (m, 4 H), 6.31 (d, J = 8.7 Hz, 1 H), 6.56 (dd, J = 8.7, 2.8 Hz, 1 H), 6.77 (d, J = 2.8 Hz, 1 H), 7.23 (d, J = 8.7 Hz, 2 H), 7.75 (d, J = 8.7 Hz, 2 H) |

TABLE 1-continued

| Compound No. | P | MS (ESI/APCI) MH+ | 1H NMR |
|---|---|---|---|
| 19 | 5-(p-tolyl)oxazole | 432 | (600 MHz, CHLOROFORM-d) δ ppm 1.08 (d, J = 6.0 Hz, 3 H), 1.36-1.46 (m, 1 H), 1.65-1.72 (m, 1 H), 1.72-1.80 (m, 1 H), 1.87-2.00 (m, 3 H), 2.06-2.13 (m, 1 H), 2.14-2.21 (m, 1 H), 2.25-2.32 (m, 1 H), 2.77-2.82 (m, 2 H), 2.91-2.98 (m, 1 H), 3.00-3.05 (m, 2 H), 3.12-3.19 (m, 1 H), 3.94-4.01 (m, 2 H), 6.31 (d, J = 8.7 Hz, 1 H), 6.58 (dd, J = 8.7, 2.8 Hz, 1 H), 6.78 (d, J = 2.8 Hz, 1 H), 7.29-7.33 (m, 2 H), 7.39 (s, 1 H), 7.74-7.79 (m, 2 H), 7.93 (s, 1 H) |
| 20 | 3-methyl-6-(p-tolyloxy)pyridazine | 473 | (600 MHz, CHLOROFORM-d) δ ppm 1.11 (d, J = 4.1 Hz, 3 H), 1.40-2.44 (m, 9 H), 2.65 (s, 3 H), 2.76-2.81 (m, 2 H), 2.95-3.02 (m, 3 H), 3.15-3.26 (m, 1 H), 3.93-4.01 (m, 2 H), 6.38 (d, J = 9.2 Hz, 1 H), 6.59 (dd, J = 9.2, 2.8 Hz, 1 H), 6.75 (d, J = 2.8 Hz, 1 H), 7.12 (d, J = 9.2 Hz, 1 H), 7.21-7.25 (m, 2 H), 7.28-7.31 (m, 2 H), 7.35 (d, J = 9.2 Hz, 1 H) |
| 21 | N,N,3-trimethylbenzamide | 436 | (600 MHz, CHLOROFORM-d) δ ppm 1.10 (d, J = 6.0 Hz, 3 H), 1.37-1.52 (m, 1 H), 1.63-2.03 (m, 5 H), 2.06-2.41 (m, 3 H), 2.73-2.83 (m, 2 H), 2.91-3.25 (m, 10 H), 3.92-4.03 (m, 2 H), 6.31 (d, J = 8.7 Hz, 1 H), 6.53-6.60 (m, 1 H), 6.77 (d, J = 2.8 Hz, 1 H), 7.23-7.32 (m, 2 H), 7.44-7.57 (m, 2 H) |
| 22 | 3-methoxytoluene | 395 | (600 MHz, CHLOROFORM-d) δ ppm 1.11 (d, J = 6.0 Hz, 3 H), 1.38-2.42 (m, 9 H), 2.77-2.83 (m, 2 H), 2.95-3.05 (m, 3 H), 3.17-3.23 (m, 1 H), 3.80 (s, 3 H), 3.93-4.02 (m, 2 H), 6.31 (d, J = 8.7 Hz, 1 H), 6.58 (dd, J = 8.7, 3.0 Hz, 1 H), 6.75-6.78 (m, 2 H), 6.80-6.84 (m, 1 H), 6.93-6.97 (m, 1 H), 7.37-7.42 (m, 1 H) |
| 23 | 2-methoxytoluene | 395 | (600 MHz, CHLOROFORM-d) δ ppm 1.14 (d, J = 6.4 Hz, 3 H), 1.40-2.46 (m, 9 H), 2.72-2.85 (m, 2 H), 2.94-3.08 (m, 3 H), 3.18-3.29 (m, 1 H), 3.73 (s, 3 H), 3.92-4.00 (m, 2 H), 6.21 (d, J = 8.7 Hz, 1 H), 6.54 (dd, J = 8.7, 2.8 Hz, 1 H), 6.75 (d, J = 2.8 Hz, 1 H), 7.01-7.07 (m, 2 H), 7.14-7.18 (m, 1 H), 7.38-7.44 (m, 1 H) |
| 24 | 3-fluorotoluene | 383 | (600 MHz, CHLOROFORM-d) δ ppm 1.11 (d, J = 5.0 Hz, 3 H), 1.36-2.39 (m, 9 H), 2.75-2.83 (m, 2 H), 2.91-3.06 (m, 3 H), 3.12-3.27 (m, 1 H), 3.95-4.02 (m, 2 H), 6.29 (d, J = 9.2 Hz, 1 H), 6.59 (dd, J = 9.2, 2.8 Hz, 1 H), 6.78 (d, J = 2.8 Hz, 1 H), 6.97-7.00 (m, 1 H), 7.02-7.06 (m, 1 H), 7.09-7.14 (m, 1 H), 7.43-7.48 (m, 1 H) |
| 25 | 2,5-dimethoxytoluene | 425 | (600 MHz, CHLOROFORM-d) δ ppm 1.03-1.19 (m, 3 H), 1.39-2.45 (m, 9 H), 2.72-2.86 (m, 2 H), 2.92-3.05 (m, 3 H), 3.12-3.28 (m, 1 H), 3.71 (s, 3 H), 3.84 (s, 3 H), 3.92-4.02 (m, 2 H), 6.26 (d, J = 9.2 Hz, 1 H), 6.54-6.58 (m, 2 H), 6.59 (d, J = 2.3 Hz, 1 H), 6.75 (d, J = 2.8 Hz, 1 H), 7.06 (d, J = 8.7 Hz, 1 H) |
| 26 | 3-fluoro-5-methoxytoluene | 413 | (600 MHz, CHLOROFORM-d) δ ppm 1.12 (d, J = 6.4 Hz, 3 H), 1.38-2.43 (m, 9 H), 2.76-2.81 (m, 2 H), 2.95-3.03 (m, 3 H), 3.17-3.24 (m, 1 H), 3.79 (s, 3 H), 3.95-4.02 (m, 2 H), 6.34 (d, J = 9.2 Hz, 1 H), 6.56-6.62 (m, 3 H), 6.65-6.69 (m, 1 H), 6.77 (d, J = 2.8 Hz, 1 H) |
| 27 | 3,5-difluorotoluene | 401 | (600 MHz, CHLOROFORM-d) δ ppm 1.04-1.17 (m, 3 H), 1.38-2.41 (m, 9 H), 2.76-2.82 (m, 2 H), 2.92-3.06 (m, 3 H), 3.14-3.26 (m, 1 H), 3.95-4.03 (m, 2 H), 6.33 (d, J = 8.7 Hz, 1 H), 6.62 (dd, J = 8.7, 2.8 Hz, 1 H), 6.78 (d, J = 2.8 Hz, 1 H), 6.79-6.89 (m, 3 H) |

TABLE 1-continued

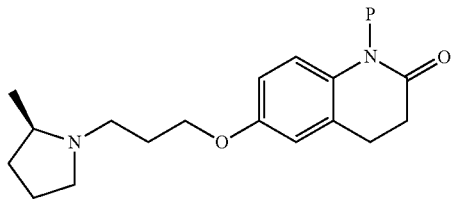

| Compound No. | P | MS (ESI/APCI) MH+ | ¹H NMR |
|---|---|---|---|
| 28 | 3,4-difluorophenyl | 401 | (600 MHz, CHLOROFORM-d) δ ppm 1.03-1.19 (m, 3 H), 1.34-2.46 (m, 9 H), 2.73-2.87 (m, 2 H), 2.93-3.06 (m, 3 H), 3.15-3.29 (m, 1 H), 3.91-4.07 (m, 2 H), 6.28 (d, J = 9.2 Hz, 1 H), 6.60 (dd, J = 9.2, 2.8 Hz, 1 H), 6.78 (d, J = 2.8 Hz, 1 H), 6.97-7.02 (m, 1 H), 7.07-7.13 (m, 1 H), 7.24-7.31 (m, 1 H) |
| 29 | 2,5-difluorophenyl | 401 | (600 MHz, CHLOROFORM-d) δ ppm 1.13 (d, J = 6.0 Hz, 3 H), 1.37-2.28 (m, 9 H), 2.75-2.86 (m, 2 H), 2.93-3.09 (m, 3 H), 3.14-3.26 (m, 1 H), 3.93-4.05 (m, 2 H), 6.27 (d, J = 8.9 Hz, 1 H), 6.61 (dd, J = 8.9, 2.8 Hz, 1 H), 6.79 (d, J = 2.8 Hz, 1 H), 6.97-7.05 (m, 2 H), 7.21-7.31 (m, 1 H) |
| 30 | 4-chloro-2-fluorophenyl | 417 | (600 MHz, CHLOROFORM-d) δ ppm 1.09 (d, J = 6.4 Hz, 3 H), 1.35-2.37 (m, 9 H), 2.77-2.83 (m, 2 H), 2.92-2.99 (m, 1 H), 2.99-3.06 (m, 2 H), 3.14-3.20 (m, 1 H), 3.94-4.03 (m, 2 H), 6.27 (d, J = 8.7 Hz, 1 H), 6.61 (dd, J = 8.7, 2.8 Hz, 1 H), 6.79 (d, J = 2.8 Hz, 1 H), 7.19-7.31 (m, 3 H) |
| 31 | 3-chloro-5-cyanophenyl | 424 | (600 MHz, CHLOROFORM-d) δ ppm 1.08 (d, J = 6.0 Hz, 3 H), 1.36-2.35 (m, 9 H), 2.74-2.82 (m, 2 H), 2.92-2.99 (m, 1 H), 2.99-3.05 (m, 2 H), 3.14-3.19 (m 1 H), 3.96-4.03 (m, 2 H), 6.26 (d, J = 8.7 Hz, 1 H), 6.63 (dd, J = 8.7, 2.8 Hz, 1 H), 6.80 (d, J = 2.8 Hz, 1 H), 7.48-7.50 (m, 1 H), 7.53-7.54 (m, 1 H), 7.63-7.66 (m, 1 H) |
| 32 | 2-methyl-5-cyanophenyl | 404 | (600 MHz, CHLOROFORM-d) δ ppm 1.05-1.19 (m, 3 H), 1.38-2.40 (m, 9 H), 2.61 (s, 3 H), 2.76-2.84 (m, 2 H), 2.91-3.07 (m, 3 H), 3.13-3.26 (m, 1 H), 3.96-4.02 (m, 2 H) 6.23 (d, J = 8.7 Hz, 1 H), 6.59 (dd, J = 8.7, 2.8 Hz, 1 H), 6.79 (d, J = 2.8 Hz, 1 H), 7.38 (dd, J = 8.3, 2.3 Hz, 1 H), 7.44 (d, J = 8.3 Hz, 1 H), 7.50 (d, J = 2.3 Hz, 1 H) |
| 33 | 2-methoxy-5-cyanophenyl | 420 | (600 MHz, CHLOROFORM-d) δ ppm 1.12 (d, J = 6.0 Hz, 3 H), 1.40-2.44 (m, 9 H), 2.76-2.82 (m, 2 H), 2.95-3.05 (m, 3 H), 3.16-3.25 (m, 1 H), 3.94-4.03 (m, 5 H), 6.25 (d, J = 8.7 Hz, 1 H), 6.60 (dd, J = 8.7, 2.8 Hz, 1 H), 6.78 (d, J = 2.8 Hz, 1 H), 7.08 (d, J = 8.7 Hz, 1 H), 7.42-7.47 (m, 2 H) |
| 34 | 2-pyridyl | 366 | (600 MHz, CHLOROFORM-d) δ ppm 1.10 (d, J = 6.0 Hz, 3 H), 1.38-1.49 (m, 1 H), 1.57-1.85 (m, 2 H), 1.87-2.03 (m, 3 H), 2.05-2.25 (m, 2 H), 2.26-2.37 (m, 1 H), 2.77-2.83 (m, 2 H), 2.92-3.00 (m, 1 H), 3.01-3.07 (m, 2 H), 3.13-3.23 (m, 1 H), 3.93-4.02 (m, 2 H), 6.21 (d, J = 9.2 Hz, 1 H), 6.57-6.62 (m, 1 H), 6.78 (d, J = 2.8 Hz, 1 H), 7.31-7.36 (m, 1 H), 7.39 (d, J = 8.3 Hz, 1 H), 7.85-7.90 (m, 1 H), 8.62-8.66 (m, 1 H) |
| 35 | 3-pyridyl | 366 | (600 MHz, CHLOROFORM-d) δ ppm 1.09 (d, J = 5.0 Hz, 3 H), 1.43 (br. s., 1 H), 1.60 (br. s., 5 H), 2.07-2.36 (m, 3 H), 2.79-2.84 (m, 2 H), 2.92-3.00 (m, 1 H), 3.01-3.07 (m, 2 H), 3.17 (br. s., 1 H), 3.95-4.03 (m, 2 H), 6.26 (d, J = 8.7 Hz, 1 H), 6.60 (dd, J = 8.7, 2.8 Hz, 1 H), 6.80 (d, J = 2.8 Hz, 1 H), 7.44 (dd, J = 7.8, 4.6 Hz, 1 H), 7.61-7.65 (m, 1 H), 8.51 (d, J = 3.2 Hz, 1 H), 8.62-8.65 (m, 1 H) |
| 36 | 5-pyrimidinyl | 367 | (600 MHz, CHLOROFORM-d) δ ppm 1.09 (d, J = 6.0 Hz, 3 H), 1.35-1.48 (m, 1 H), 1.57-2.06 (m, 5 H), 2.07-2.25 (m, 2 H), 2.25-2.36 (m, 1 H), 2.78-2.87 (m 2 H), 2.91-3.01 (m, 1 H), 3.01-3.10 (m, 2 H), 3.14-3.22 (m, 1 H), 3.93-4.06 (m, 2 H), 6.29 (d, J = 8.7 Hz, 1 H), 6.63 (dd, J = 9.2, 2.8 Hz, 1 H), 6.82 (d, J = 2.8 Hz, 1 H), 8.71 (s, 2 H), 9.21 (s, 1 H) |

TABLE 1-continued

[Structure: (S)-2-methylpyrrolidine connected via propyl-O linker to 6-position of 1-P-3,4-dihydroquinolin-2(1H)-one]

| Compound No. | P | MS (ESI/APCI) MH+ | ¹H NMR |
|---|---|---|---|
| 37 | 3-quinolinyl | 416 | (600 MHz, CHLOROFORM-d) δ ppm 1.09 (d, J = 5.0 Hz, 3 H), 1.37-2.39 (m, 9 H), 2.82-2.88 (m, 2 H), 2.92-3.00 (m, 1 H), 3.04-3.09 (m, 2 H), 3.13-3.22 (m, 1 H), 3.92-4.01 (m, 2 H), 6.28 (d, J = 8.7 Hz, 1 H), 6.55 (dd, J = 8.7, 2.8 Hz, 1 H), 6.80 (d, J = 2.8 Hz, 1 H), 7.55-7.60 (m, 1 H), 7.73-7.77 (m, 1 H), 7.80-7.83 (m, 1 H), 8.11 (d, J = 2.3 Hz, 1 H), 8.14 (d, J = 8.3 Hz, 1 H), 8.72 (d, J = 2.3 Hz, 1 H) |
| 38 | 6-quinolinyl | 416 | (600 MHz, CHLOROFORM-d) δ ppm 1.10-1.21 (m, 3 H), 1.42-2.56 (m, 9 H), 2.81-2.88 (m, 2 H), 2.97-3.12 (m, 3 H), 3.17-3.35 (m, 1 H), 3.93-4.04 (m, 2 H), 6.28 (d, J = 8.7 Hz, 1 H), 6.55 (dd, J = 8.7, 2.8 Hz, 1 H), 6.80 (d, J = 2.8 Hz, 1 H), 7.42-7.45 (m, 1 H), 7.52-7.53 (m, 1 H), 7.54 (d, J = 2.3 Hz, 1 H), 7.76-7.78 (m, 1 H), 8.13-8.17 (m, 1 H), 8.21 (d, J = 8.7 Hz, 1 H), 8.93-8.98 (m, 1 H) |
| 39 | 1,5-naphthyridinyl | 417 | (600 MHz, CHLOROFORM-d) δ ppm 1.09-1.21 (m, 3 H), 1.41-2.44 (m, 9 H), 2.85-2.93 (m, 2 H), 2.98-3.07 (m, 1 H), 3.08-3.15 (m, 2 H), 3.20-3.27 (m 1 H), 3.96-4.04 (m 2 H), 6.34 (d, J = 8.7 Hz, 1 H), 6.58 (dd, J = 8.7, 2.8 Hz, 1 H), 6.83-6.85 (m, 1 H), 7.70 (dd, J = 8.7, 4.1 Hz, 1 H), 8.36-8.37 (m, 1 H), 8.45-8.48 (m, 1 H), 8.84 (d, J = 2.3 Hz, 1 H), 9.01-9.03 (m, 1 H) |
| 40 | 1,6-naphthyridinyl | 417 | (600 MHz, CHLOROFORM-d) δ ppm 1.04-1.14 (m, 3 H), 1.37-1.48 (m, 1 H), 1.61-2.34 (m, 8 H), 2.83-2.89 (m, 2 H), 2.92-3.00 (m, 1 H), 3.07-3.20 (m 3 H), 3.94-4.03 (m, 2 H), 6.27 (d, J = 9.2 Hz, 1 H), 6.58 (dd, J = 8.9, 3.0 Hz, 1 H), 6.82 (d, J = 2.8 Hz, 1 H), 7.64-7.71 (m, 2 H), 8.38 (d, J = 9.2 Hz, 1 H), 8.55 (d, J = 8.7 Hz, 1 H), 9.01-9.05 (m, 1 H) |
| 41 | 5-(N-Boc)indolyl | 504 | (600 MHz, CHLOROFORM-d) δ ppm 1.08 (d, J = 6.0 Hz, 3 H), 1.35-2.31 (m, 18 H), 2.80-2.86 (m, 2 H), 2.91-2.98 (m, 1 H), 3.00-3.08 (m, 2 H), 3.12-3.20 (m, 1 H), 3.92-4.01 (m, 2 H) 6.54 (dd J = 8.7, 2.8 Hz, 1 H), 6.57 (d, J = 3.7 Hz, 1 H), 6.78 (d, J = 2.8 Hz, 1 H), 7.14 (dd, J = 8.7, 1.8 Hz, 1 H), 7.44 (d, J = 2.3 Hz, 1 H), 7.65 (d, J = 3.2 Hz, 1 H), 8.24 (br. s., 1 H) |
| 42 | 3-(N-Boc)indolyl | 504 | (600 MHz, CHLOROFORM-d) δ ppm 1.08 (d, J = 6.0 Hz, 3 H), 1.36-2.32 (m, 18 H), 2.80-2.99 (m, 2 H), 3.01-3.11 (m, 2 H), 3.12-3.20 (m, 1 H), 3.93-4.02 (m, 2 H), 6.48-6.54 (m, 1 H), 6.54-6.58 (m, 1 H), 6.81 (d J = 2.8 Hz, 1 H), 7.07-7.13 (m, 1 H), 7.16 (t, J = 7.1 Hz, 1 H), 7.34 (t, J = 7.8 Hz, 1 H), 7.72 (s, 1 H), 8.23 (br. s., 1 H) |
| 43 | 2,3-dihydrobenzo[1,4]dioxinyl | 423 | (600 MHz, CHLOROFORM-d) δ ppm 1.09 (d, J = 5.5 Hz, 3 H), 1.37-2.39 (m, 9 H), 2.75-2.81 (m, 2 H), 2.91-3.04 (m, 3 H), 3.12-3.23 (m, 1 H), 3.94-4.01 (m, 2 H), 4.26-4.32 (m, 4 H), 6.35 (d, J = 9.2 Hz, 1 H), 6.59 (dd, J = 9.2, 2.8 Hz, 1 H), 6.69 (dd, J = 8.3, 2.5 Hz, 1 H), 6.74-6.77 (m, 2 H), 6.95 (d, J = 8.3 Hz, 1 H) |
| 44 | benzo[1,3]dioxolyl | 409 | (600 MHz, CHLOROFORM-d) δ ppm 1.11 (d, J = 6.0 Hz, 3 H), 1.39-2.43 (m, 9 H), 2.75-2.81 (m, 2 H), 2.94-3.03 (m, 3 H), 3.17-3.23 (m, 1 H), 3.94-4.02 (m, 2 H), 6.03 (s, 2 H), 6.36 (d, J = 8.7 Hz, 1 H), 6.59 (dd, J = 8.9, 3.0 Hz, 1 H), 6.67-6.70 (m, 2 H), 6.76 (d, J = 2.8 Hz, 1 H), 6.89-6.91 (m, 1 H) |
| 45 | 2,3-dihydrobenzofuranyl | 407 | (600 MHz, CHLOROFORM-d) δ ppm 1.08-1.19 (m, 3 H), 1.40-2.42 (m, 9 H), 2.75-2.83 (m, 2 H), 2.96-3.06 (m, 3 H), 3.23-3.28 (m, 3 H), 3.95-4.03 (m, 2 H), 4.63 (t, J = 8.7 Hz, 2 H), 6.34 (d, J = 8.7 Hz 1 H), 6.58 (dd J = 8.7, 2.8 Hz, 1 H), 6.76 (d, J = 2.8 Hz, 1 H), 6.86 (d, J = 8.5 Hz, 1 H), 6.93 (dd, J = 8.5, 2.1 Hz, 1 H), 7.01-7.06 (m, 1 H) |

TABLE 1-continued

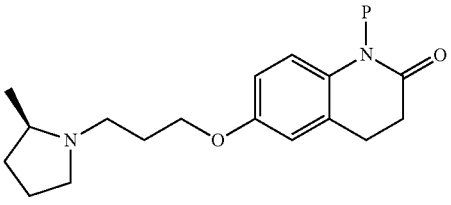

| Compound No. | P | MS (ESI/APCI) MH+ | ¹H NMR |
|---|---|---|---|
| 46 | 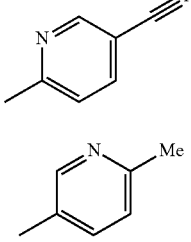 | 391 | (600 MHz, CHLOROFORM-d) δ ppm 1.09 (d, J = 6.0 Hz, 3 H), 1.36-1.47 (m, 1 H), 1.65-1.83 (m, 2 H), 1.87-2.00 (m, 3 H), 2.06-2.22 (m, 2 H), 2.23-2.34 (m, 1 H), 2.76-2.83 (m, 2 H), 2.91-3.06 (m, 3 H), 3.12-3.20 (m, 1 H), 3.95-4.03 (m, 2 H), 6.32 (d, J = 8.7 Hz, 1 H), 6.64 (dd, J = 8.7, 2.8 Hz, 1 H), 6.80 (d, J = 2.8 Hz, 1 H), 7.65 (d, J = 8.3 Hz, 1 H), 8.10 (dd, J = 8.5, 2.5 Hz, 1 H), 8.83 (d, J = 2.3 Hz, 1 H) |
| 47 | 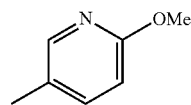 | 380 | (600 MHz, CHLOROFORM-d) δ ppm 1.13 (d, J = 6.0 Hz, 3 H), 1.44-1.54 (m, 1 H), 1.67-1.76 (m, 1 H), 1.77-1.87 (m, 1 H), 1.90-2.07 (m, 3 H), 2.17-2.34 (m, 2 H), 2.37-2.49 (m, 1 H), 2.59 (s, 3 H), 2.72-2.81 (m, 2 H), 2.96-3.04 (m, 3 H), 3.20-3.26 (m, 1 H), 3.90-4.00 (m, 2 H), 6.24 (d, J = 8.7 Hz, 1 H), 6.55 (dd, J = 8.7, 2.8 Hz, 1 H), 6.75 (d, J = 2.8 Hz, 1 H), 7.26 (d, J = 8.3 Hz, 1 H), 7.46 (dd, J = 8.3, 2.3 Hz, 1 H), 8.33 (d, J = 2.3 Hz, 1 H) |
| 48 | 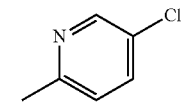 | 396 | (600 MHz, CHLOROFORM-d) δ ppm 1.11 (d, J = 6.0 Hz, 3 H), 1.39-2.41 (m, 9 H), 2.77-2.81 (m, 2 H), 2.95-3.03 (m, 3 H), 3.17-3.22 (m, 1 H), 3.94-3.99 (m, 5 H), 6.30 (d J = 8.7 Hz, 1 H), 6.58 (dd, J = 8.7, 2.8 Hz, 1 H), 6.76 (d, J = 2.8 Hz, 1 H), 6.85 (d, J = 8.7 Hz, 1 H), 7.43 (dd, J = 8.7, 2.3 Hz, 1 H), 8.02 (d, J = 2.3 Hz, 1 H) |
| 49 | 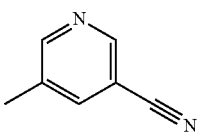 | 400 | (600 MHz, CHLOROFORM-d) δ ppm 1.12 (d, J = 6.0 Hz, 3 H), 1.40-1.52 (m, 1 H), 1.66-2.03 (m, 5 H), 2.10-2.29 (m, 2 H), 2.30-2.44 (m, 1 H), 2.74-2.84 (m, 2 H), 2.93-3.08 (m, 3 H), 3.16-3.26 (m, 1 H), 3.94-4.03 (m, 2 H), 6.24 (d, J = 9.2 Hz, 1 H), 6.61 (dd, J = 8.9, 2.5 Hz, 1 H), 6.78 (d, J = 2.3 Hz, 1 H), 7.36 (d, J = 8.3 Hz, 1 H), 7.78-7.87 (m, 1 H), 8.56 (s, 1 H) |
| 50 | 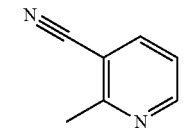 | 391 | (600 MHz, CHLOROFORM-d) δ ppm 1.09 (d, J = 6.0 Hz, 3 H), 1.36-1.48 (m, 1 H), 1.64-2.05 (m, 5 H), 2.05-2.36 (m, 3 H), 2.77-2.85 (m, 2 H), 2.91-3.10 (m, 3 H), 3.12-3.22 (m, 1 H), 3.95-4.05 (m, 2 H), 6.26 (d, J = 9.2 Hz, 1 H), 6.64 (dd, J = 8.7, 2.8 Hz, 1 H), 6.82 (d, J = 2.8 Hz, 1 H), 7.92-8.00 (m, 1 H), 8.73 (d, J = 2.3 Hz, 1 H), 8.86 (d, J = 1.8 Hz, 1 H) |
| 51 | 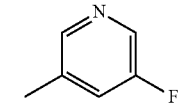 | 391 | (600 MHz, CHLOROFORM-d) δ ppm 1.03-1.43 (m, 4 H), 1.56-2.69 (m, 8 H), 2.79-2.93 (m, 2 H), 3.01-3.27 (m, 3 H), 3.33-3.69 (m, 1 H), 3.94-4.09 (m, 2 H), 6.18 (d, J = 8.7 Hz, 1 H), 6.60 (dd, J = 8.9, 3.0 Hz, 1 H), 6.81 (d, J = 2.8 Hz, 1 H), 7.51 (dd, J = 7.8, 5.0 Hz, 1 H), 8.16 (dd, J = 7.8, 2.3 Hz, 1 H), 8.80-8.89 (m, 1 H) |
| 52 | 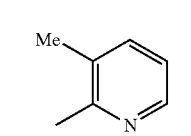 | 384 | (600 MHz, CHLOROFORM-d) δ ppm 1.12 (d, J = 6.0 Hz, 3 H), 1.40-1.51 (m, 1 H), 1.65-1.86 (m, 2 H), 1.88-2.07 (m, 3 H), 2.08-2.28 (m, 2 H), 2.29-2.42 (m, 1 H), 2.75- 2.85 (m, 2 H), 2.94-3.09 (m, 3 H), 3.15-3.26 (m, 1 H), 3.93-4.05 (m, 2 H), 6.29 (d, J = 8.7 Hz, 1 H), 6.62 (dd, J = 8.7, 2.8 Hz, 1 H), 6.81 (d, J = 2.8 Hz, 1 H), 7.42 (dt, J = 8.7, 2.3 Hz, 1 H), 8.35 (s, 1 H), 8.51 (d, J = 2.8 Hz, 1 H) |
| 53 | 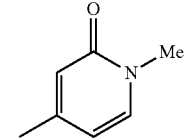 | 380 | (600 MHz, CHLOROFORM-d) δ ppm 1.08-1.43 (m, 4 H), 1.75-2.54 (m, 8 H), 2.63 (s, 3 H), 2.81 (dd, J = 8.5, 6.2 Hz, 2 H), 2.98-3.16 (m, 3 H), 3.26-3.45 (m, 1 H), 3.95-4.05 (m, 2 H), 6.26-6.31 (m, 1 H), 6.54-6.61 (m, 1 H), 6.76-6.81 (m, 1 H), 7.30 (d, J = 8.3 Hz, 1 H), 7.49 (dd, J = 8.3, 2.3 Hz, 1 H), 8.37 (d, J = 2.3 Hz, 1 H) |
| 54 |  | 396 | (600 MHz, CHLOROFORM-d) δ ppm 1.08 (d, J = 6.0 Hz, 3 H), 1.34-2.34 (m, 9 H), 2.71-2.79 (m, 2 H), 2.91-3.01 (m, 3 H), 3.12-3.20 (m, 1 H), 3.58 (s, 3 H), 3.96-4.03 (m, 2 H), 6.11 (dd, J = 8.7, 2.3 Hz, 1 H), 6.54 (d, J = 2.3 Hz, 1 H), 6.58 (d, J = 8.7 Hz, 1 H), 6.65 (dd, J = 8.7, 2.8 Hz, 1 H), 6.77 (d, J = 2.8 Hz, 1 H), 7.37 (d, J = 8.7 Hz, 1 H) |

TABLE 1-continued

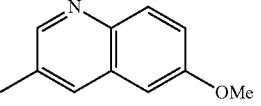

| Compound No. | P | MS (ESI/APCI) MH+ | 1H NMR |
|---|---|---|---|
| 55 | ![structure with N, methyl, OMe] | 446 | (600 MHz, CHLOROFORM-d) δ ppm 1.09-1.18 (m, 3 H), 1.39-2.44 (m, 9 H), 2.84-2.89 (m, 2 H), 2.96-3.03 (m, 1 H), 3.06-3.10 (m, 2 H), 3.18-3.25 (m, 1 H), 3.93 (s, 3 H), 3.95-4.03 (m, 2 H), 6.29-6.33 (m, 1 H), 6.57 (dd, J = 8.7, 2.8 Hz, 1 H), 6.81-6.83 (m, 1 H), 7.06-7.08 (m, 1 H), 7.39-7.43 (m, 1 H), 8.00-8.02 (m, 1 H), 8.03-8.06 (m, 1 H), 8.58 (d, J = 2.3 Hz, 1 H) |

Example 2

Preparation of 1-(1H-indol-5-yl)-6-{3-[(2R)-2-methylpyrrolidin-1-yl]propoxy}-3,4-dihydroquinolin-2(1H)-one (Compound No. 56)

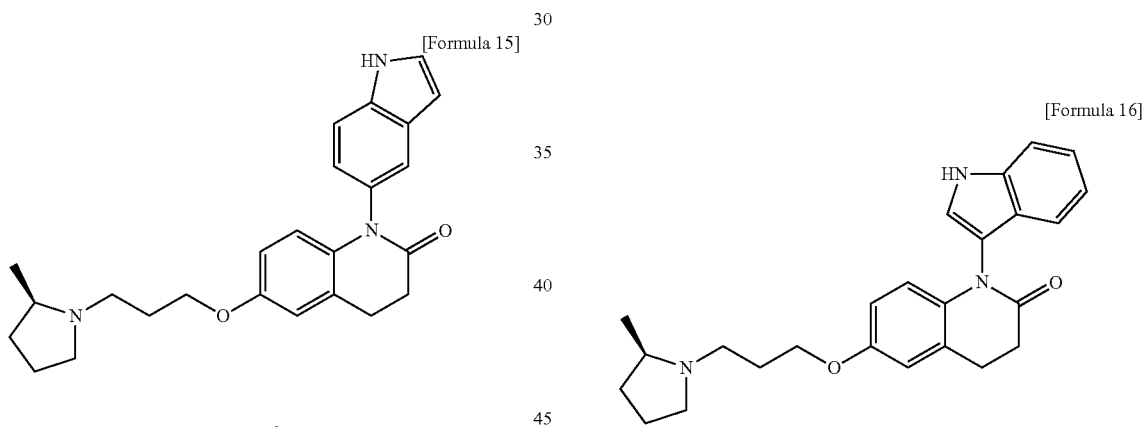

[Formula 15]

To a solution of tert-butyl 5-[6-{3-[(2R)-2-methylpyrrolidin-1-yl]propoxy}-2-oxo-3,4-dihydroquinolin-1(2H)-yl]-1H-indole-1-carboxylate (Compound No. 41) prepared in the same manner as shown in Example 1 (0.050 g) in methanol (0.19 mL), water (0.3 mL) and potassium carbonate (0.041 g) were added and stirred at 80° C. for 2 hours. The reaction mixture was concentrated under reduced pressure, and the resulting residue was purified by NH-type preparative TLC (on three plates of 0.25 mm thickness, developing solvent: ethyl acetate) to give the titled compound (0.0090 g, 2.2%) as a colorless amorphous substance.

$^1$H NMR (600 MHz, CHLOROFORM-d) δ ppm 1.08 (d, J=6.4 Hz, 3 H), 1.36-1.46 (m, 1 H), 1.59-1.82 (m, 2 H), 1.85-2.01 (m, 3 H), 2.06-2.13 (m, 1 H), 2.14-2.21 (m, 1 H), 2.23-2.32 (m, 1 H), 2.79-2.87 (m, 2 H), 2.91-2.99 (m, 1 H), 3.01-3.09 (m, 2 H), 3.12-3.19 (m, 1 H), 3.90-4.01 (m, 2 H), 6.30 (d, J=9.2 Hz, 1 H), 6.50-6.56 (m, 2 H), 6.77 (d, J=3.2 Hz, 1 H), 6.95-7.01 (m, 1 H), 7.20-7.24 (m, 1 H), 7.43 (d, J=8.3 Hz, 1 H), 7.49 (d, J=1.8 Hz, 1 H), 8.46 (br. s., 1 H)

MS (ESI/APCI Dual) (Positive) m/z; 404 (M+H)+

Example 3

Preparation of 1-(1H-indol-3-yl)-6-{3-[(2R)-2-methylpyrrolidin-1-yl]propoxy}-3,4-dihydroquinolin-2(1H)-one (Compound No. 57)

[Formula 16]

The same procedure as shown in Example 2 was repeated to give the titled compound, except that tert-butyl 5-[6-{3-[(2R)-2-methylpyrrolidin-1-yl]propoxy}-2-oxo-3,4-dihydroquinolin-1(2H)-yl]-1H-indole-1-carboxylate (Compound No. 41) was replaced by tert-butyl 3-[6-{3-[(2R)-2-methylpyrrolidin-1-yl]propoxy}-2-oxo-3,4-dihydroquinolin-1(2H)-yl]-1H-indole-1-carboxylate (Compound No. 42).

$^1$H NMR (600 MHz, CHLOROFORM-d) δ ppm 1.08 (d, J=6.0 Hz, 3 H), 1.35-1.46 (m, 1 H), 1.62-1.82 (m, 2 H), 1.86-2.00 (m, 3 H), 2.06-2.13 (m, 1 H), 2.13-2.21 (m, 1 H), 2.22-2.32 (m, 1 H), 2.82-2.90 (m, 2 H), 2.90-2.99 (m, 1 H), 3.01-3.11 (m, 2 H), 3.11-3.19 (m, 1 H), 3.92-4.01 (m, 2 H), 6.47-6.51 (m, 1 H), 6.51-6.56 (m, 1 H), 6.80 (d, J=2.8 Hz, 1 H), 7.04-7.10 (m, 1 H), 7.16-7.24 (m, 2 H), 7.30 (d, J=2.8 Hz, 1 H), 7.38-7.44 (m, 1 H), 8.29 (br. s., 1 H)

MS (ESI/APCI Dual) (Positive) m/z; 404 (M+H)+

Example 4

Preparation of 6-[(1-cyclobutylpiperidin-4-yl)oxy]-3,4-dihydro-2H-1,3'-biquinolin-2-one (Compound No. 58)

(1) Preparation of 6-(1-cyclobutylpiperidin-4-yloxy)-3,4-dihydroquinolin-2(1H)-one

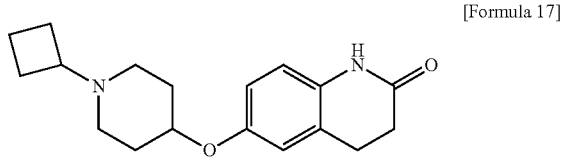 [SMILES: O=C1CCc2cc(OC3CCN(C4CCC4)CC3)ccc2N1]

[Formula 17]

Under a nitrogen atmosphere, to a solution of 6-hydroxy-3,4-dihydroquinolin-2(1H)-one (5.00 g) and N-cyclobutyl-4-hydroxypiperidine (which can be synthesized as described in WO2005/108384) (7.10 g) in tetrahydrofuran (50 mL), diethyl azodicarboxylate (40% in toluene, 16.7 mL) was added dropwise under ice cooling. After completion of the dropwise addition, the reaction mixture was warmed to room temperature and stirred for 40 hours. The reaction mixture was concentrated under reduced pressure, and the resulting residue was purified by silica gel column chromatography (eluting solvent: chloroform/methanol=95/5) to give the titled compound (2.30 g, 25%) as a colorless powder.

(2) Preparation of 6-[(1-cyclobutylpiperidin-4-yl)oxy]-3,4-dihydro-2H-1,3'-biquinolin-2-one (Compound No. 58)

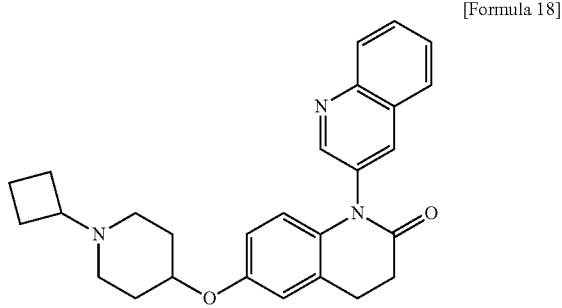 [SMILES: O=C1CCc2cc(OC3CCN(C4CCC4)CC3)ccc2N1c1cnc2ccccc2c1]

[Formula 18]

A suspension of 6-(1-cyclobutylpiperidin-4-yloxy)-3,4-dihydroquinolin-2(1H)-one synthesized in Example 4-(1) (0.10 g), 3-bromoisoquinoline (0.10 g), rac-trans-N,N'-dimethylcyclohexane-1,2-diamine (0.047 g), copper iodide (0.016 g) and cesium carbonate (0.22 g) in toluene (1 mL) was stirred at 110° C. for 3 hours. The reaction mixture was cooled to room temperature, diluted with chloroform and filtered to remove insoluble materials. The filtrate was concentrated under reduced pressure, and the resulting residue was purified by NH-type silica gel column chromatography (eluting solvent: hexane/ethyl acetate=4/1 to 1/4) and OH-type preparative TLC (on two plates of 1 mm thickness, developing solvent: chloroform/methanol=4/1) to give the titled compound (0.061 g, 44%) as a colorless amorphous substance.

$^1$H NMR (600 MHz, CHLOROFORM-d) δ ppm 1.54-2.24 (m, 12 H), 2.54-2.80 (m, 3 H), 2.82-2.91 (m, 2 H), 3.04-3.12 (m, 2 H), 4.17-4.31 (m, 1 H), 6.30 (d, J=8.7 Hz, 1 H), 6.57 (dd, J=8.7, 2.8 Hz, 1 H), 6.83 (d, J=2.8 Hz, 1 H), 7.56-7.64 (m, 1 H), 7.74-7.81 (m, 1 H), 7.84 (d, J=8.3 Hz, 1 H), 8.10-8.22 (m, 2 H), 8.74 (d, J=2.3 Hz, 1 H)

MS (ESI/APCI Dual) (Positive) m/z; 428 (M+H)$^+$

Example 5

Preparation of 6-[(1-tert-butylpiperidin-4-yl)oxy]-3,4-dihydro-2H-1,3'-biquinolin-2-one (Compound No. 59)

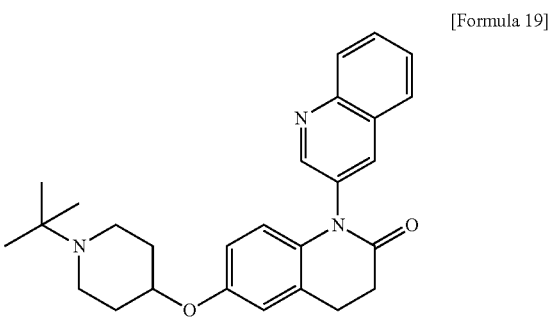 [SMILES: CC(C)(C)N1CCC(Oc2ccc3c(c2)CCC(=O)N3c2cnc3ccccc3c2)CC1]

[Formula 19]

The same procedure as shown in Example 4 was repeated to give the titled compound, except that N-cyclobutyl-4-hydroxypiperidine was replaced by 1-tert-butyl-4-hydroxypiperidine (which can be synthesized as described in Journal of Organic Chemistry, 2005, vol. 70, pp. 1930-1933).

$^1$H NMR (600 MHz, CHLOROFORM-d) δ ppm 0.82-2.61 (m, 14 H), 2.81-3.22 (m, 7 H), 4.09-4.43 (m, 1 H), 6.31 (d, J=8.7 Hz, 1 H), 6.57 (dd, J=8.7, 2.8 Hz, 1 H), 6.83 (d, J=2.8 Hz, 1 H), 7.57-7.63 (m, 1 H), 7.75-7.81 (m, 1 H), 7.84 (d, J=8.3 Hz, 1 H), 8.10-8.20 (m, 2 H), 8.74 (d, J=2.3 Hz, 1H)

MS (ESI/APCI Dual) (Positive) m/z; 430 (M+H)$^+$

Example 6

Preparation of 6-[(1-cyclobutylpiperidin-4-yl)oxy]-1-(4-fluorophenyl)-3,4-dihydroquinolin-2(1H)-one (Compound No. 60)

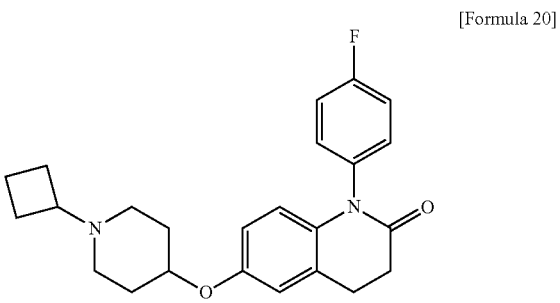 [SMILES: O=C1CCc2cc(OC3CCN(C4CCC4)CC3)ccc2N1c1ccc(F)cc1]

[Formula 20]

The same procedure as shown in Example 4 was repeated to give the titled compound, except that 3-bromoquinoline was replaced by 4-fluoroiodobenzene.

$^1$H NMR (600 MHz, CHLOROFORM-d) δ ppm 1.59-2.23 (m, 12 H), 2.49-2.87 (m, 5 H), 2.91-3.17 (m, 2 H), 4.16-4.26 (m, 1 H), 6.24 (d, J=8.7 Hz, 1 H), 6.58 (dd, J=8.7, 2.8 Hz, 1 H), 6.77 (d, J=2.8 Hz, 1 H), 7.12-7.22 (m, 4 H)

MS (ESI/APCI Dual) (Positive) m/z; 395 (M+H)$^+$

Example 6-2

Preparation of 6-[(1-cyclobutylpiperidin-4-yl)oxy]-1-(4-fluorophenyl)-3,4-dihydroquinolin-2(1H)-one hydrochloride (hydrochloride salt of Compound No. 60)

To a solution of 6-[(1-cyclobutylpiperidin-4-yl)oxy]-1-(4-fluorophenyl)-3,4-dihydroquinolin-2(1H)-one (Compound No. 60) prepared in Example 6 (0.90 g) in a mixture of ethyl acetate (10 mL) and ethanol (2 mL), 4N hydrochloric acid in ethyl acetate (1.14 mL) was added and stirred at room temperature for 3 hours. The reaction mixture was concentrated under reduced pressure, followed by addition of isopropanol (7 mL) and ethanol (2 mL) to the residue. The mixture was stirred for 5 minutes while heating in an oil bath (110° C.), and then stirred while cooling to room temperature. The precipitate was collected by filtration and dried to give the titled compound (0.93 g, 95%) as a colorless crystal.

$^1$H NMR (600 MHz, DMSO-$d_6$) δ ppm 1.63-1.79 (m, 2 H), 1.81-1.92 (m, 1 H), 1.95-2.03 (m, 1 H), 2.06-2.20 (m, 4 H), 2.28-2.41 (m, 2 H), 2.65-2.70 (m, 2 H), 2.76-2.93 (m, 2 H), 2.99-3.02 (m, 2 H), 3.15-3.23 (m, 1 H), 3.33-3.40 (m, 1 H), 3.54-3.74 (m, 1 H), 4.40-4.68 (m, 1 H), 6.14 (s, 1 H), 6.67-6.77 (m, 1 H), 6.94-7.03 (m, 1 H), 7.26-7.30 (m, 2 H), 7.32-7.37 (m, 2 H), 10.82-10.93 (m, 1 H)

MS (ESI/APCI Dual) (Positive) m/z; 395 (M+H)$^+$
Melting point>250° C.

The same procedures as shown in Examples 4 to 6 were repeated to prepare the compounds listed below:
6-[(1-tert-butylpiperidin-4-yl)oxy]-1-phenyl-3,4-dihydroquinolin-2(1H)-one (Compound No. 61);
4-{6-[(1-tert-butylpiperidin-4-yl)oxy]-2-oxo-3,4-dihydroquinolin-1(2H)-yl}benzonitrile (Compound No. 62);
3-{6-[(1-tert-butylpiperidin-4-yl)oxy]-2-oxo-3,4-dihydroquinolin-1(2H)-yl}benzonitrile (Compound No. 63);
6-[(1-tert-butylpiperidin-4-yl)oxy]-1-(5-fluoropyridin-3-yl)-3,4-dihydroquinolin-2(1H)-one (Compound No. 64);
6-[(1-tert-butylpiperidin-4-yl)oxy]-1-(6-methoxypyridin-3-yl)-3,4-dihydroquinolin-2(1H)-one (Compound No. 65);
6-[(1-tert-butylpiperidin-4-yl)oxy]-1-(4-fluorophenyl)-3,4-dihydroquinolin-2(1H)-one (Compound No. 66);
6-[(1-cyclobutylpiperidin-4-yl)oxy]-1-(6-methoxypyridin-3-yl)-3,4-dihydroquinolin-2(1H)-one (Compound No. 67);
6-[(1-cyclobutylpiperidin-4-yl)oxy]-1-(3,5-difluorophenyl)-3,4-dihydroquinolin-2(1H)-one (Compound No. 68);
6-[(1-cyclobutylpiperidin-4-yl)oxy]-1-(3-fluorophenyl)-3,4-dihydroquinolin-2(1H)-one (Compound No. 69);
1-(4-chlorophenyl)-6-[(1-cyclobutylpiperidin-4-yl)oxy]-3,4-dihydroquinolin-2(1H)-one (Compound No. 70);
6-[(1-cyclobutylpiperidin-4-yl)oxy]-1-(5-fluoropyridin-3-yl)-3,4-dihydroquinolin-2(1H)-one (Compound No. 71);
6-[(1-cyclobutylpiperidin-4-yl)oxy]-1-phenyl-3,4-dihydroquinolin-2(1H)-one (Compound No. 72);
4-{6-[(1-cyclobutylpiperidin-4-yl)oxy]-2-oxo-3,4-dihydroquinolin-1(2H)-yl}benzonitrile (Compound No. 73); and
3-{6-[(1-cyclobutylpiperidin-4-yl)oxy]-2-oxo-3,4-dihydroquinolin-1(2H)-yl}benzonitrile (Compound No. 74).

The structural formulae as well as physical and chemical data of Compound Nos. 61 to 74 are shown in Table 2.

TABLE 2

| Compound No. | R$^5$ | P | MS (ESI/APCI) MH$^+$ | $^1$H NMR |
|---|---|---|---|---|
| 61 | tert-butyl | phenyl | 379 | (600 MHz, CHLOROFORM-d) δ ppm 1.07 (s, 9 H), 1.71-1.80 (m, 2 H), 1.92-2.00 (m, 2 H), 2.34-2.41 (m, 2 H), 2.76-2.88 (m, 4 H), 2.98-3.03 (m, 2 H), 4.13-4.20 (m, 1 H), 6.24 (d, J = 8.7 Hz, 1 H), 6.56 (dd, J = 8.9, 3.0 Hz, 1 H), 6.75-6.78 (m, 1 H), 7.22 (d, J = 8.3 Hz, 2 H), 7.36-7.42 (m, 1 H), 7.45-7.51 (m, 2 H) |
| 62 | tert-butyl | 4-CN-phenyl | 404 | (600 MHz, CHLOROFORM-d) δ ppm 1.08 (s, 9 H), 1.72-1.81 (m, 2 H), 1.92-2.01 (m, 2 H), 2.34-2.43 (m, 2 H), 2.74-2.89 (m, 4 H), 2.96-3.04 (m, 2 H), 4.14-4.23 (m, 1 H), 6.23 (d, J = 8.7 Hz, 1 H), 6.59 (dd, J = 8.7, 2.8 Hz, 1 H), 6.79 (d, J = 2.8 Hz, 1 H), 7.39 (d, J = 8.7 Hz, 2 H), 7.76 (d, J = 8.7 Hz, 2 H) |
| 63 | tert-butyl | 3-CN-phenyl | 404 | (600 MHz, CHLOROFORM-d) δ ppm 1.08 (s, 9 H), 1.71-1.81 (m, 2 H), 1.92-2.02 (m, 2 H), 2.33-2.43 (m, 2 H), 2.75-2.89 (m, 4 H), 2.96-3.06 (m, 2 H), 4.14-4.23 (m, 1 H), 6.20 (d, J = 8.7 Hz, 1 H), 6.57-6.63 (m, 1 H), 6.79 (d, J = 2.8 Hz, 1 H), 7.51 (d. J = 8.3 Hz, 1 H), 7.54-7.62 (m, 2 H), 7.67 (d, J = 7.8 Hz, 1 H) |
| 64 | tert-butyl | 5-F-pyridin-3-yl | 398 | (600 MHz, CHLOROFORM-d) δ ppm 1.08 (s, 9 H), 1.72-1.83 (m, 2 H), 1.91-2.02 (m, 2 H), 2.32-2.45 (m, 2 H), 2.76-2.89 (m, 4 H), 2.98-3.07 (m, 2 H), 4.15-4.24 (m, 1 H), 6.27 (d, J = 8.7 Hz, 1 H), 6.58-6.64 (m, 1 H), 6.79 (d, J = 2.8 Hz, 1 H), 7.38-7.45 (m, 1 H), 8.34 (s, 1 H), 8.50 (d, J = 2.3 Hz, 1 H) |

TABLE 2-continued

[Structure: R⁵-N(piperidine)-O-[6-position of 3,4-dihydroquinolin-2(1H)-one with N-P substituent]]

| Compound No. | R⁵ | P | MS (ESI/APCI) MH⁺ | ¹H NMR |
|---|---|---|---|---|
| 65 | tert-butyl (Me,Me,Me) | 5-methyl-2-methoxypyridin-yl (OMe) | 410 | (600 MHz, CHLOROFORM-d) δ ppm 1.08 (s, 9 H), 1.72-1.82 (m, 2 H), 1.92-2.01 (m, 2 H), 2.33-2.42 (m, 2 H), 2.75-2.88 (m, 4 H), 2.97-3.03 (m, 2 H), 3.97 (s, 3 H), 4.14-4.21 (m, 1 H), 6.30 (d, J = 8.7 Hz, 1 H), 6.56-6.61 (m, 1 H), 6.77 (d, J = 2.8 Hz, 1 H), 6.86 (d, J = 8.7 Hz, 1 H), 7.43 (dd, J = 8.7, 2.8 Hz, 1 H), 8.03 (d, J = 2.3 Hz, 1 H) |
| 66 | tert-butyl (Me,Me,Me) | 4-fluorophenyl (F) | 397 | (600 MHz, CHLOROFORM-d) δ ppm 0.94-1.23 (m, 9 H), 1.66-2.13 (m, 4 H), 2.32-2.49 (m, 2 H), 2.72-3.07 (m, 6 H), 4.09-4.31 (m, 1 H), 6.20-6.27 (m, 1 H), 6.52-6.60 (m, 1 H), 6.73-6.77 (m, 1 H), 7.12-7.21 (m, 4 H) |
| 67 | cyclobutyl | 5-methyl-2-methoxypyridin-yl (OMe) | 408 | (600 MHz, CHLOROFORM-d) δ ppm 1.61-1.74 (m, 2 H), 1.74-1.82 (m, 2 H), 1.82-1.91 (m, 2 H), 1.91-1.98 (m, 2 H), 1.99-2.06 (m, 2 H), 2.06-2.16 (m, 2 H), 2.55-2.64 (m, 2 H), 2.68-2.75 (m, 1 H), 2.77-2.83 (m, 2 H), 2.98-3.03 (m, 2 H), 3.97 (s, 3 H), 4.18-4.25 (m, 1 H), 6.30 (d, J = 8.7 Hz, 1 H), 6.59 (dd, J = 8.9, 3.0 Hz, 1 H), 6.77 (d, J = 3.2 Hz, 1 H), 6.85 (d, J = 8.7 Hz, 1 H), 7.43 (dd, J = 8.7, 2.8 Hz, 1 H), 8.03 (d, J = 2.8 Hz, 1 H) |
| 68 | cyclobutyl | 3,5-difluorophenyl (F, F) | 413 | (600 MHz, CHLOROFORM-d) δ ppm 1.61-2.21 (m, 12 H), 2.54-2.67 (m, 2 H), 2.68-2.81 (m, 3 H), 2.96-3.02 (m, 2 H), 4.18-4.28 (m, 1 H), 6.31 (d, J = 8.7 Hz, 1 H), 6.61 (dd, J = 8.7, 2.8 Hz, 1 H), 6.75-6.89 (m, 4 H) |
| 69 | cyclobutyl | 3-fluorophenyl (F) | 395 | (600 MHz, CHLOROFORM-d) δ ppm 1.54-2.24 (m, 12 H), 2.52-2.67 (m, 2 H), 2.68-2.83 (m, 3 H), 2.96-3.03 (m, 2 H), 4.17-4.28 (m, 1 H), 6.27 (d, J = 8.7 Hz, 1 H), 6.58 (dd, J = 8.7, 2.8 Hz, 1 H), 6.77 (d, J = 2.8 Hz, 1 H), 6.94-6.99 (m, 1 H), 7.03 (d, J = 7.8 Hz, 1 H), 7.07-7.14 (m, 1 H), 7.40-7.48 (m, 1 H) |
| 70 | cyclobutyl | 4-chlorophenyl (Cl) | 411 | (600 MHz, CHLOROFORM-d) δ ppm 1.60-2.19 (m, 12 H), 2.54-2.66 (m, 2 H), 2.67-2.81 (m, 3 H), 2.97-3.02 (m, 2 H), 4.17-4.26 (m, 1 H), 6.26 (d, J = 8.7 Hz, 1 H), 6.58 (dd, J = 8.7, 2.8 Hz, 1 H), 6.76 (d, J = 2.8 Hz, 1 H), 7.14-7.19 (m, 2 H), 7.42-7.48 (m, 2 H) |
| 71 | cyclobutyl | 5-fluoropyridin-3-yl | 396 | (600 MHz, CHLOROFORM-d) δ ppm 1.65-2.26 (m, 12 H), 2.55-2.88 (m, 5 H), 3.00-3.11 (m, 2 H), 4.20-4.32 (m, 1 H), 6.31 (d, J = 8.7 Hz, 1 H), 6.64 (dd, J = 8.9, 3.0 Hz, 1 H), 6.82 (d, J = 2.8 Hz, 1 H), 7.37-7.53 (m, 1 H), 8.37 (s, 1 H), 8.53 (d, J = 2.8 Hz, 1 H) |
| 72 | cyclobutyl | phenyl | 377 | (600 MHz, CHLOROFORM-d) δ ppm 1.60-2.21 (m, 12 H), 2.54-2.82 (m, 5 H), 2.97-3.04 (m, 2 H), 4.17-4.26 (m, 1 H), 6.25 (d, J = 8.7 Hz, 1 H), 6.56 (dd, J = 8.9, 3.0 Hz, 1 H), 6.76 (d, J = 2.8 Hz, 1 H), 7.11-7.24 (m, 2 H), 7.37-7.41 (m, 1 H), 7.46-7.51 (m, 2 H) |
| 73 | cyclobutyl | 4-cyanophenyl (CN) | 402 | (600 MHz, CHLOROFORM-d) δ ppm 1.61-2.21 (m, 12 H), 2.54-2.81 (m, 5 H), 2.97-3.03 (m, 2 H), 4.23 (br. s, 1 H), 6.24 (d, J = 8.7 Hz, 1 H), 6.59 (dd, J = 9.2, 2.8 Hz, 1 H), 6.78 (d, J = 2.8 Hz, 1 H), 7.36-7.40 (m, 2 H), 7.74-7.78 (m, 2 H) |
| 74 | cyclobutyl | 3-cyanophenyl (CN) | 402 | (600 MHz, CHLOROFORM-d) δ ppm 1.55-2.26 (m, 12 H), 2.52-2.83 (m, 5 H), 2.97-3.04 (m, 2 H), 4.18-4.28 (m, 1 H), 6.20 (d, J = 8.7 Hz, 1 H), 6.60 (dd, J = 8.7, 2.8 Hz, 1 H), 6.79 (d, J = 2.8 Hz, 1 H), 7.49-7.53 (m, 1 H), 7.55-7.62 (m, 2 H), 7.68 (d, J = 7.8 Hz, 1 H) |

Example 7

Preparation of 1-(4-fluorophenyl)-6-{[1-(propan-2-yl)piperidin-4-yl]oxy}-3,4-dihydroquinolin-2(1H)-one (Compound No. 75)

(1) Preparation of tert-butyl 4-(2-oxo-1,2,3,4-tetrahydroquinolin-6-yloxy)piperidine-1-carboxylate

[Formula 21]

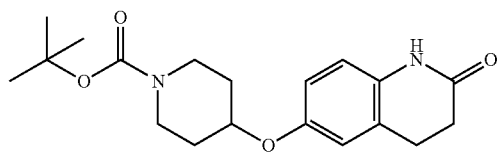

A suspension of 6-hydroxy-3,4-dihydroquinolin-2(1H)-one (5.0 g), tert-butyl 4-(methanesulfonyloxy)piperidine-1-carboxylate (13 g) and potassium carbonate (5.1 g) in N,N-dimethylformamide (30 mL) was stirred at 100° C. for 20 hours. The reaction mixture was cooled to room temperature, diluted with water and extracted with chloroform. The organic layer was washed with brine and concentrated under reduced pressure. The resulting residue was purified by NH-type silica gel column chromatography (eluting solvent: chloroform/hexane=4/1) to give the titled compound (6.9 g, 65%) as a colorless solid.

(2) Preparation of tert-butyl 4-(1-(4-fluorophenyl)-2-oxo-1,2,3,4-tetrahydroquinolin-6-yloxy)piperidine-1-carboxylate

[Formula 22]

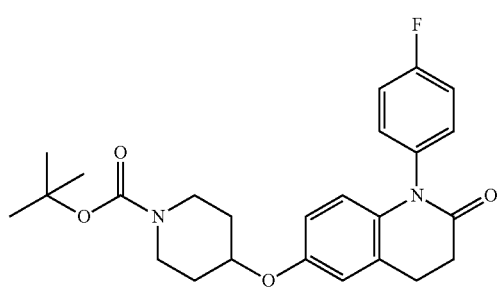

A suspension of tert-butyl 4-(2-oxo-1,2,3,4-tetrahydroquinolin-6-yloxy)piperidine-1-carboxylate prepared in Example 7-(1) (3.0 g), 1-fluoro-4-iodobenzene (2.9 g), rac-trans-N,N'-dimethylcyclohexane-1,2-diamine (1.2 g), copper iodide (0.41 g) and cesium carbonate (5.6 g) in toluene (8.0 mL) was stirred at 100° C. for 4 hours. The reaction mixture was cooled to room temperature, diluted with toluene and filtered to remove insoluble materials. The filtrate was concentrated under reduced pressure. The resulting residue was purified by silica gel column chromatography (eluting solvent: hexane/ethyl acetate=7/3 to 1/4) to give the titled compound (3.8 g, 99%) as a colorless amorphous substance.

(3) Preparation of 1-(4-fluorophenyl)-6-(piperidin-4-yloxy)-3,4-dihydroquinolin-2(1H)-one hydrochloride

[Formula 23]

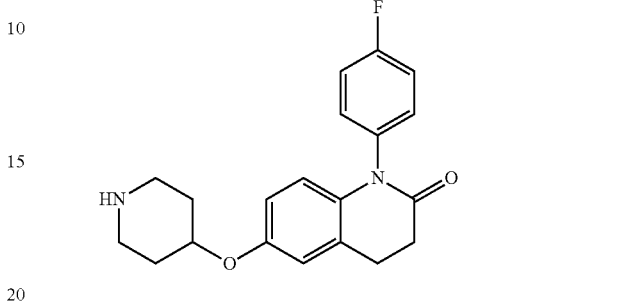

To a solution of tert-butyl 4-(1-(4-fluorophenyl)-2-oxo-1,2,3,4-tetrahydroquinolin-6-yloxy)piperidine-1-carboxylate prepared in Example 7-(2) (6.0 g) in a mixture of ethyl acetate (12 mL) and ethanol (4 mL), 4M hydrochloric acid in ethyl acetate (10 mL) was added dropwise at room temperature and stirred for 16 hours. The reaction mixture was concentrated under reduced pressure, diluted with ethyl acetate and stirred at room temperature for 1 hour. The precipitate was collected by filtration and dried to give the titled compound (5.1 g, 99%) as a colorless solid.

(4) Preparation of 1-(4-fluorophenyl)-6-{[1-(propan-2-yl)piperidin-4-yl]oxy}-3,4-dihydroquinolin-2(1H)-one (Compound No. 75)

[Formula 24]

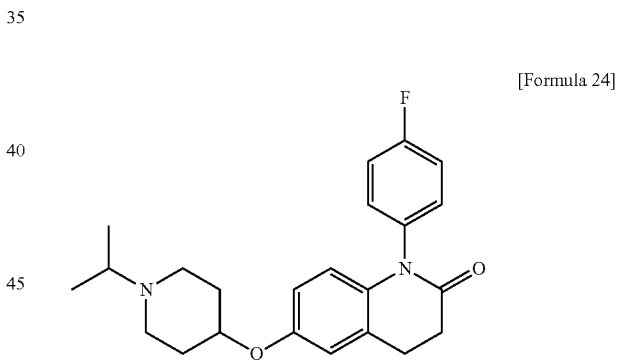

A suspension of 1-(4-fluorophenyl)-6-(piperidin-4-yloxy)-3,4-dihydroquinolin-2(1H)-one hydrochloride prepared in Example 7-(3) (0.30 g), potassium carbonate (0.55 g) and 2-iodopropane (0.68 g) in N,N-dimethylformamide (10 mL) was stirred at 100° C. for 1 hour. The reaction mixture was cooled to room temperature, diluted with water and extracted with chloroform. The organic layer was washed with brine, dried over anhydrous sodium sulfate and concentrated under reduced pressure. The resulting residue was purified by silica gel column chromatography (eluting solvent: chloroform→chloroform/methanol=4/1) to give the titled compound (0.16 g, 52%) as a colorless solid.

$^1$H NMR (600 MHz, CHLOROFORM-d) δ ppm 1.06 (d, J=6.0 Hz, 6 H), 1.80 (br. s., 2 H), 2.00 (br. s., 2 H), 2.39 (br. s., 2 H), 2.70-2.83 (m, 5 H), 2.97-3.03 (m, 2 H), 4.16-4.25 (m, 1 H), 6.24 (d, J=9.2 Hz, 1 H), 6.58 (dd, J=8.9, 3.0 Hz, 1 H), 6.77 (d, J=2.8 Hz, 1 H), 7.13-7.22 (m, 4 H)

MS (ESI/APCI Dual) (Positive) m/z; 383 (M+H)$^+$

Example 8

Preparation of 6-{[1-(cyclopropylmethyl)piperidin-4-yl]oxy}-1-(4-fluorophenyl)-3,4-dihydroquinolin-2(1H)-one (Compound No. 76)

[Formula 25]

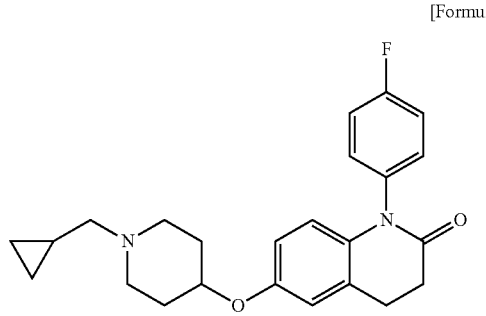

A suspension of 1-(4-fluorophenyl)-6-(piperidin-4-yloxy)-3,4-dihydroquinolin-2(1H)-one hydrochloride prepared in Example 7-(3) (0.30 g), potassium carbonate (0.55 g) and (bromomethyl)cyclopropane (0.32 g) in N,N-dimethylformamide (10 mL) was stirred at 100° C. for 6 hours. The reaction mixture was cooled to room temperature, diluted with water and extracted with chloroform. The organic layer was washed with brine, dried over anhydrous sodium sulfate and concentrated under reduced pressure. The resulting residue was purified by silica gel column chromatography (eluting solvent: chloroform→chloroform/methanol=4/1) and preparative TLC (on a single plate of 2 mm thickness, developing solvent: chloroform/methanol=9/1) to give the titled compound (0.11 g, 35%) as a colorless amorphous substance.

$^1$H NMR (600 MHz, CHLOROFORM-d) δ ppm 0.07-0.14 (m, 2 H), 0.47-0.55 (m, 2 H), 0.89 (br. s., 1 H), 1.78-1.88 (m, 2 H), 1.97-2.06 (m, 2 H), 2.22-2.50 (m, 4 H), 2.74-2.88 (m, 4 H), 2.96-3.02 (m, 2 H), 4.23 (br. s., 1 H), 6.24 (d, J=8.7 Hz, 1 H), 6.57 (dd, J=9.2, 2.8 Hz, 1 H), 6.76 (d, J=2.8 Hz, 1 H), 7.13-7.21 (m, 4 H)

MS (ESI/APCI Dual) (Positive) m/z; 395 (M+H)$^+$

Example 9

Preparation of 6-[(1-cyclopropylpiperidin-4-yl)oxy]-1-(4-fluorophenyl)-3,4-dihydroquinolin-2(1H)-one (Compound No. 77)

[Formula 26]

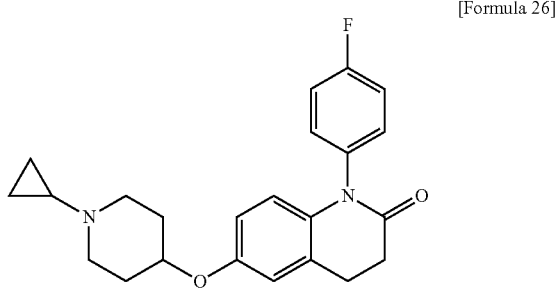 [SMILES: O=C1CCc2cc(OC3CCN(C4CC4)CC3)ccc2N1c1ccc(F)cc1]

A suspension of 1-(4-fluorophenyl)-6-(piperidin-4-yloxy)-3,4-dihydroquinolin-2(1H)-one hydrochloride prepared in Example 7-(3) (0.30 g), triethylamine (0.080 g), [(1-ethoxycyclopropyl)-oxy]trimethylsilane (0.69 g), acetic acid (0.48 g) and molecular sieves 3A (1.0 g) in methanol (10 mL) was stirred at room temperature for 1 hour, followed by addition of sodium cyanoborohydride (0.25 g) and stirring at the same temperature for 16 hours. The reaction mixture was warmed to 95° C., heated under reflux for 7 hours, and then cooled to room temperature, followed by filtration to remove insoluble materials. The filtrate was concentrated under reduced pressure, and the resulting residue was purified by silica gel column chromatography (eluting solvent: chloroform→chloroform/methanol=4/1) and preparative TLC (on a single plate of 2 mm thickness, developing solvent: chloroform/methanol=9/1) to give the titled compound (0.11 g, 37%) as a colorless amorphous substance.

$^1$H NMR (600 MHz, CHLOROFORM-d) δ ppm 0.37-0.51 (m, 4 H), 1.57-1.68 (m, 1 H), 1.71-1.84 (m, 2 H), 1.89-2.01 (m, 2 H), 2.42-2.55 (m, 2 H), 2.78-2.84 (m, 2 H), 2.90 (br. s., 2 H), 2.99-3.07 (m, 2 H), 4.19-4.28 (m, 1 H), 6.27 (d, J=8.7 Hz, 1 H), 6.57-6.63 (m, 1 H), 6.77-6.81 (m, 1 H), 7.15-7.25 (m, 4 H)

MS (ESI/APCI Dual) (Positive) m/z; 381 (M+H)$^+$

Example 10

Preparation of 1-(4-fluorophenyl)-6-[3-(pyrrolidin-1-yl)propoxy]-3,4-dihydroquinolin-2(1H)-one (Compound No. 78)

(1) Preparation of 6-(3-chloropropoxy)-3,4-dihydroquinolin-2(1H)-one

[Formula 27]

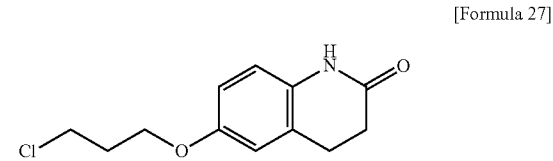 [SMILES: O=C1CCc2cc(OCCCCl)ccc2N1]

A suspension of 6-hydroxy-3,4-dihydroquinolin-2(1H)-one (50 g), cesium carbonate (150 g) and 1-bromo-3-chloropropane (58 g) in acetonitrile (300 mL) was stirred at 110° C. for 4 hours. The reaction mixture was cooled to room temperature, diluted with chloroform and filtered to remove insoluble materials. The filtrate was concentrated under reduced pressure. The resulting residue was purified by silica gel column chromatography (eluting solvent: chloroform→chloroform/methanol=4/1), and the resulting solid was subjected to recrystallization from ethanol to give the titled compound (42 g, 68%) as a colorless solid.

(2) Preparation of 6-[3-(pyrrolidin-1-yl)propoxy]-3,4-dihydroquinolin-2(1H)-one

[Formula 28]

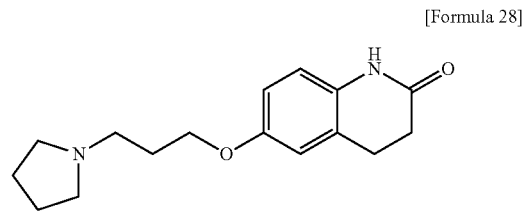 [SMILES: O=C1CCc2cc(OCCCN3CCCC3)ccc2N1]

A solution of 6-(3-chloropropoxy)-3,4-dihydroquinolin-2(1H)-one prepared in Example 10-(1) (10 g) and pyrrolidine (15 g) in 2-propanol (15 mL) was stirred at 90° C. for 2 days. The reaction mixture was cooled to room temperature, diluted with water and extracted with chloroform. The organic layer was washed with brine, dried over anhydrous sodium sulfate and concentrated under reduced pressure. The resulting residue was purified by silica gel column chromatography (eluting solvent: chloroform→chloroform/methanol=4/1), and the resulting solid was subjected to recrystallization from ethyl acetate to give the titled compound (7.5 g, 65%) as a colorless solid.

(3) Preparation of 1-(4-fluorophenyl)-6-[3-(pyrrolidin-1-yl)propoxy]-3,4-dihydroquinolin-2(1H)-one (Compound No. 78)

[Formula 29]

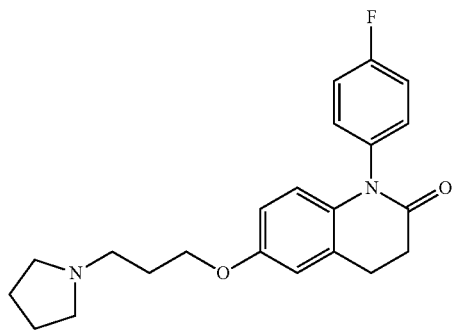

A suspension of 6-[3-(pyrrolidin-1-yl)propoxy]-3,4-dihydroquinolin-2(1H)-one prepared in Example 10-(2) (0.20 g), 1-fluoro-4-iodobenzene (0.24 g), rac-trans-N,N'-dimethylcyclohexane-1,2-diamine (0.10 g), copper iodide (0.035 g) and cesium carbonate (0.48 g) in toluene (1.0 mL) was stirred at 105° C. for 60 hours. The reaction mixture was cooled to room temperature, diluted with chloroform and filtered to remove insoluble materials. The filtrate was concentrated under reduced pressure. The resulting residue was purified by NH-type silica gel column chromatography (eluting solvent: hexane/ethyl acetate=1/1), and the resulting solid was subjected to recrystallization from a mixture of diisopropyl ether and ethyl acetate to give the titled compound (0.10 g, 37%) as a colorless solid.

$^1$H NMR (600 MHz, CHLOROFORM-d) δ ppm 1.74-1.83 (m, 4 H), 1.92-2.02 (m, 2 H), 2.51 (t, J=6.6 Hz, 4 H), 2.57-2.63 (m, 2 H), 2.76-2.82 (m, 2 H), 2.97-3.04 (m, 2 H), 3.94-4.01 (m, 2 H), 6.26 (d, J=8.7 Hz, 1 H), 6.58 (dd, J=8.9, 3.0 Hz, 1 H), 6.78 (d, J=2.8 Hz, 1 H), 7.14-7.23 (m, 4 H)

MS (ESI/APCI Dual) (Positive) m/z; 369 (M+H)$^+$

The same procedure as shown in Example 10 was repeated to prepare the compounds listed below:
1-(3-fluorophenyl)-6-[3-(pyrrolidin-1-yl)propoxy]-3,4-dihydroquinolin-2(1H)-one (Compound No. 79);
1-(3,5-difluorophenyl)-6-[3-(pyrrolidin-1-yl)propoxy]-3,4-dihydroquinolin-2(1H)-one (Compound No. 80);
1-(3,4-difluorophenyl)-6-[3-(pyrrolidin-1-yl)propoxy]-3,4-dihydroquinolin-2(1H)-one (Compound No. 81);
1-(4-fluorophenyl)-6-[3-(piperidin-1-yl)propoxy]-3,4-dihydroquinolin-2(1H)-one (Compound No. 82);
6-[3-(diethylamino)propoxy]-1-(4-fluorophenyl)-3,4-dihydroquinolin-2(1H)-one (Compound No. 83); and
6-{3-[(2R,5R)-2,5-dimethylpyrrolidin-1-yl]propoxy}-1-(4-fluorophenyl)-3,4-dihydroquinolin-2(1H)-one (Compound No. 84).

The structural formulae as well as physical and chemical data of Compound Nos. 79 to 84 are shown in Table 3.

TABLE 3

| Compound No. | NR$^3$NR$^4$ | P | MS (ESI/APCI) MH$^+$ | $^1$H NMR |
|---|---|---|---|---|
| 79 | pyrrolidine | 3-fluorophenyl | 369 | (600 MHz, CHLOROFORM-d) δ ppm 1.76-1.94 (m, 4 H), 1.99-2.17 (m, 2 H), 2.53-2.85 (m, 8 H), 2.97-3.06 (m, 2 H), 4.00 (t, J = 6.2 Hz, 2 H), 6.29 (d, J = 9.2 Hz, 1 H), 6.59 (dd, J = 8.7, 2.8 Hz, 1 H), 6.76-6.81 (m, 1 H), 6.96-7.01 (m, 1 H), 7.01-7.06 (m, 1 H), 7.09-7.15 (m, 1 H), 7.42-7.49 (m, 1 H) |
| 80 | pyrrolidine | 3,5-difluorophenyl | 387 | (600 MHz, CHLOROFORM-d) δ ppm 1.74-1.89 (m, 4 H), 1.96-2.09 (m, 2 H), 2.46-2.80 (m, 8 H), 2.96-3.02 (m, 2 H), 3.99 (t, J = 6.4 Hz, 2 H), 6.32 (d, J = 8.7 Hz, 1 H), 6.58-6.63 (m, 1 H), 6.75-6.89 (m, 4 H) |
| 81 | pyrrolidine | 3,4-difluorophenyl | 387 | (600 MHz, CHLOROFORM-d) δ ppm 1.76-1.89 (m, 4 H), 1.96-2.09 (m, 2 H), 2.47-2.82 (m, 8 H), 2.97-3.04 (m, 2 H), 3.98 (t, J = 6.4 Hz, 2 H), 6.27 (d, J = 8.7 Hz, 1 H), 6.59 (dd, J = 8.7, 2.8 Hz, 1 H), 6.77 (d, J = 2.8 Hz, 1 H), 6.95-7.02 (m, 1 H), 7.05-7.12 (m, 1 H), 7.22-7.30 (m, 1 H) |

TABLE 3-continued

[Structure with R³R⁴N-propyl-O-linked to 3,4-dihydroquinolin-2(1H)-one with N-P substituent]

| Compound No. | NR³NR⁴ | P | MS (ESI/APCI) MH⁺ | ¹H NMR |
|---|---|---|---|---|
| 82 | piperidinyl | 4-F-phenyl-CH₂ | 383 | (600 MHz, CHLOROFORM-d) δ ppm 1.40-1.48 (m, 2 H), 1.51-1.61 (m, 4 H), 1.89-1.97 (m, 2 H), 2.30-2.46 (m, 6 H), 2.76-2.81 (m, 2 H), 2.97-3.03 (m, 2 H), 3.95 (t, J = 6.4 Hz, 2 H), 6.25 (d, J = 8.7 Hz, 1 H), 6.57 (dd, J = 8.7, 2.8 Hz, 1 H), 6.76 (d, J = 2.8 Hz, 1 H), 7.13-7.22 (m, 4 H) |
| 83 | Me(Et)N-CH₂ type (diethylamino-methyl) | 4-F-phenyl-CH₂ | 371 | (600 MHz, CHLOROFORM-d) δ ppm 1.02 (t, J = 7.1 Hz, 6 H), 1.86-1.93 (m, 2 H), 2.49-2.61 (m, 6 H), 2.75-2.83 (m, 2 H), 2.98-3.04 (m, 2 H), 3.96 (t, J = 6.4 Hz, 2 H), 6.26 (d, J = 9.2 Hz, 1 H), 6.58 (dd, J = 9.2, 2.8 Hz, 1 H), 6.77 (d, J = 2.8 Hz, 1 H), 7.14-7.23 (m, 4 H) |
| 84 | 2,5-dimethylpyrrolidinyl | 4-F-phenyl-CH₂ | 397 | (600 MHz. CHLOROFORM-d) δ ppm 0.96 (d, J = 6.0 Hz, 6 H), 1.32-1.41 (m, 2 H), 1.86-2,05 (m, 4 H), 2.48-2.56 (m, 1 H), 2.69-2.82 (m, 3 H), 2.97-3.09 (m, 4 H), 3.92-4.03 (m, 2 H), 6.26 (d, J = 8.7 Hz, 1 H), 6.59 (dd, J = 8.9, 3.0 Hz, 1 H), 6.78 (d, J = 2.8 Hz, 1 H), 7.14-7.24 (m, 4 H) |

Example 11

Preparation of 8-chloro-1-(4-fluorophenyl)-6-{3-[(2R)-2-methylpyrrolidin-1-yl]propoxy}-3,4-dihydroquinolin-2(1H)-one (Compound No. 85)

(1) Preparation of 8-chloro-6-hydroxy-3,4-dihydroquinolin-2(1H)-one

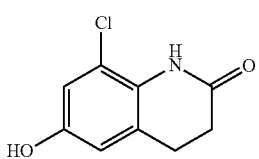

[Formula 30]

A suspension of 3-chloro-N-(2-fluoro-4-methoxyphenyl) propaneamide (1.0 g, synthesized from 3-chlorobutyryl chloride and 2-fluoro-4-methoxyaniline) and aluminum chloride (5.0 g) in n-heptane (2.0 mL) was stirred at 110° C. for 3 days. The reaction mixture was diluted with chloroform, followed by addition of ice-cold water under ice cooling. After stirring at room temperature for 2 hours, the organic layer and the aqueous layer were separated. The aqueous layer was extracted with chloroform, and the organic layers were combined, dried over anhydrous magnesium sulfate and concentrated under reduced pressure. The resulting residue was purified by silica gel column chromatography (eluting solvent: hexane/ethyl acetate=3/2) and NH-type silica gel column chromatography (eluting solvent: chloroform/methanol=99/1 to 9/1) to give the titled compound (0.059 g, 7%) as a light-yellow solid.

(2) Preparation of 8-chloro-1-(4-fluorophenyl)-6-{3-[(2R)-2-methylpyrrolidin-1-yl]propoxy}-3,4-dihydroquinolin-2(1H)-one (Compound No. 85)

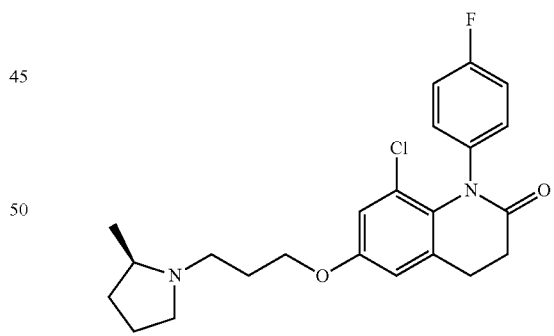

[Formula 31]

The same procedure as shown in Example 1 was repeated to give the titled compound, except that 6-hydroxy-3,4-dihydroquinolin-2(1H)-one was replaced by 8-chloro-6-hydroxy-3,4-dihydroquinolin-2(1H)-one prepared in Example 11-(1), and 4-iodobenzonitrile was replaced by 4-fluoroiodobenzene.

¹H NMR (600 MHz, CHLOROFORM-d) δ ppm 1.11-1.28 (m, 3 H), 1.43-2.57 (m, 9 H), 2.66-2.74 (m, 2 H), 2.90-3.14 (m, 3 H), 3.31 (br. s., 1 H), 3.96-4.04 (m, 2 H), 6.69-6.75 (m, 2 H), 6.99-7.05 (m, 2 H), 7.12-7.18 (m, 2 H)

MS (ESI/APCI Dual) (Positive) m/z; 417 (M+H)⁺

Example 12

Preparation of 1-(4-fluorophenyl)-8-methyl-6-{3-[(2R)-2-methylpyrrolidin-1-yl]propoxy}-3,4-dihydroquinolin-2(1H)-one (Compound No. 86)

(1) Preparation of 6-hydroxy-8-methyl-3,4-dihydroquinolin-2(1H)-one

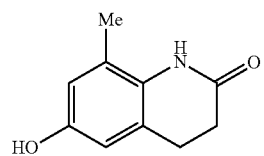

[Formula 32]

A suspension of 3-chloro-N-(4-methoxy-2-methylphenyl)propaneamide (0.50 g, synthesized from 3-chlorobutyryl chloride and 4-methoxy-2-methylaniline) and aluminum chloride (1.4 g) in n-heptane (4.0 mL) was stirred at 110° C. for 4 days. The reaction mixture was diluted with chloroform, followed by addition of ice-cold water under ice cooling. After stirring at room temperature for 1 hour, the organic layer and the aqueous layer were separated. The aqueous layer was extracted with ethyl acetate, and the organic layers were combined, dried over anhydrous magnesium sulfate and concentrated under reduced pressure. The resulting residue was purified by silica gel column chromatography (eluting solvent: chloroform/methanol=10/0 to 97/3) to give the titled compound (0.166 g, 39%) as a light-brown solid.

(2) Preparation of 1-(4-fluorophenyl)-8-methyl-6-{3-[(2R)-2-methylpyrrolidin-1-yl]propoxy}-3,4-dihydroquinolin-2(1H)-one (Compound No. 86)

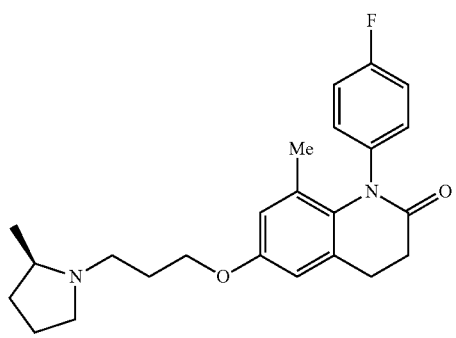

[Formula 33]

The same procedure as shown in Example 1 was repeated to give the titled compound, except that 6-hydroxy-3,4-dihydroquinolin-2(1H)-one was replaced by 6-hydroxy-8-methyl-3,4-dihydroquinolin-2(1H)-one prepared in Example 12-(1), and 4-iodobenzonitrile was replaced by 4-fluoroiodobenzene.

$^1$H NMR (600 MHz, CHLOROFORM-d) δ ppm 1.11-1.30 (m, 3 H), 1.48-2.59 (m, 12 H), 2.64-2.71 (m, 2 H), 2.86-2.93 (m, 2 H), 3.00-3.13 (m, 1 H), 3.22-3.41 (m, 1 H), 3.95-4.05 (m, 2 H), 6.45-6.50 (m, 1 H), 6.60-6.66 (m, 1 H), 6.96-7.05 (m, 2 H), 7.13-7.21 (m, 2 H)

MS (ESI/APCI Dual) (Positive) m/z; 397 (M+H)$^+$

Test Example 1

H3 Receptor Binding Test

A membrane preparation of human H3 receptor-expressing CHO-K1 cells (Perkin Elmer, ES-392-M400UA, 15 µg protein/200 µl), R(−)-α-methyl[$^3$H]histamine (Amersham, TRK-1017, specific activity: 1.74 TBq/mmol, 1 nM) and a test drug were reacted at room temperature for 1 hour. After completion of the reaction, the reaction mixture was subjected to suction filtration through a 0.3% polyethyleneimine-treated glass filter (GF/C). The glass filter was washed five times with 50 mM Tris-HCl washing solution (pH 7.4) containing 5 mM EDTA. After washing, the glass filter was dried and a scintillator was added thereto, followed by measurement of radioactivity on the filter using a liquid scintillation counter.

Binding of R(−)-α-methyl[$^3$H]histamine in the presence of 10 µM R(−)-α-methylhistamine was defined as non-specific binding, and the difference between total binding and non-specific binding of R(−)-α-methyl[$^3$H]histamine was defined as specific binding of R(−)-α-methyl[$^3$H]histamine. A fixed concentration (1 nM) of R(−)-α-methyl[$^3$H]histamine was reacted under the above conditions with each test drug at various concentrations to obtain an inhibition curve. The inhibition curve was used to determine the concentration (IC$_{50}$) of each test drug required for 50% inhibition of R(−)-α-methyl[$^3$H]histamine binding. The IC$_{50}$ values of the compounds prepared in the examples are shown in Table 4.

TABLE 4

| Compound No. | IC$_{50}$ (nM) |
|---|---|
| 1 | 4.4 |
| 2 | 0.79 |
| 3 | 1.0 |
| 4 | 2.7 |
| 5 | 3.9 |
| 6 | 1.1 |
| 7 | 1.6 |
| 8 | 1.6 |
| 9 | 3.5 |
| 10 | 1.6 |
| 11 | 2.9 |
| 12 | 0.68 |
| 13 | 8.3 |
| 14 | 5.7 |
| 15 | 3.6 |
| 16 | 11 |
| 17 | 41 |
| 18 | 20 |
| 19 | 4.0 |
| 20 | 1.0 |
| 21 | 26 |
| 22 | 1.6 |
| 23 | 1.2 |
| 24 | 0.92 |
| 25 | 2.0 |
| 26 | 2.4 |
| 27 | 2.1 |
| 28 | 1.0 |
| 29 | 1.0 |
| 30 | 1.1 |
| 31 | 1.9 |
| 32 | 2.7 |
| 33 | 4.0 |
| 34 | 8.1 |
| 35 | 2.2 |
| 36 | 5.8 |
| 37 | 3.1 |

TABLE 4-continued

| Compound No. | IC$_{50}$ (nM) |
|---|---|
| 38 | 2.9 |
| 39 | 4.4 |
| 40 | 20 |
| 41 | 53 |
| 42 | 34 |
| 43 | 2.2 |
| 44 | 1.2 |
| 45 | 2.3 |
| 46 | 22 |
| 47 | 2.9 |
| 48 | 8.7 |
| 49 | 4.0 |
| 50 | 5.7 |
| 51 | 13 |
| 52 | 1.2 |
| 53 | 1.6 |
| 54 | 4.8 |
| 55 | 5.4 |
| 56 | 1.3 |
| 57 | 0.76 |
| 58 | 1.6 |
| 59 | 8.5 |
| 60 | 0.80 |
| 61 | 2.4 |
| 62 | 4.9 |
| 63 | 6.1 |
| 64 | 5.3 |
| 65 | 12 |
| 66 | 3.7 |
| 67 | 2.7 |
| 68 | 0.72 |
| 69 | 0.65 |
| 70 | 0.75 |
| 71 | 1.4 |
| 72 | 0.60 |
| 73 | 1.0 |
| 74 | 1.3 |
| 75 | 1.4 |
| 76 | 9.8 |
| 77 | 2.1 |
| 78 | 13 |
| 79 | 17 |
| 80 | 22 |
| 81 | 18 |
| 82 | 9.1 |
| 83 | 13 |
| 84 | 5.0 |
| 85 | 11 |
| 86 | 12 |

Test Example 2

[$^{35}$S]GTP-γ-S Binding Test

The same human H3 receptor membrane preparation as used in Test Example 1 (7.5 μg protein/200 μl), 3 μM GDP, 10 nM R(−)-α-methylhistamine and a test compound were reacted at 30° C. for 20 minutes. After completion of the reaction, [$^{35}$S]GTP-γ-S (0.2 nM) was added and reacted for an additional 30 minutes. After completion of the reaction, the reaction mixture was subjected to suction filtration through a glass filter (GF/C). The glass filter was washed three times with 20 mM HEPES washing solution (pH 7.4) containing 100 mM sodium chloride and 3 mM magnesium chloride. After washing, the glass filter was dried and a scintillator was added thereto, followed by measurement of radioactivity on the filter using a liquid scintillation counter.

Binding of [$^{35}$S]GTP-γ-S in the absence of R(−)-α-methylhistamine was defined as non-specific binding, and the difference between total binding in the presence of R(−)-α-methylhistamine and non-specific binding was defined as specific binding of [$^{35}$S]GTP-γ-S. Fixed concentrations of [$^{35}$S]GTP-γ-S (0.2 nM) and R(−)-α-methylhistamine (10 nM) were reacted under the above conditions with each test drug at various concentrations to obtain an inhibition curve. The inhibition curve was used to determine the concentration (IC$_{50}$) of each test drug required for 50% inhibition of [$^{35}$S] GTP-γ-S binding. As a result, Compound No. 6 was found to have an IC$_{50}$ value of 0.28 nM, Compound No. 12 was found to have an IC$_{50}$ value of 0.21 nM, Compound No. 13 was found to have an IC$_{50}$ value of 0.62 nM, Compound No. 58 was found to have an IC$_{50}$ value of 0.40 nM, Compound No. 60 was found to have an IC$_{50}$ value of 0.23 nM, Compound No. 69 was found to have an IC$_{50}$ value of 0.20 nM, Compound No. 71 was found to have an IC$_{50}$ value of 0.26 nM, Compound No. 72 was found to have an IC$_{50}$ value of 0.16 nM, and Compound No. 73 was found to have an IC$_{50}$ value of 0.23 nM.

INDUSTRIAL APPLICABILITY

The present invention enables the provision of pharmaceutical preparations which have a strong inhibitory effect against binding to histamine H3 receptors and are useful for prevention or treatment of histamine H3 receptor-mediated disorders such as dementia, Alzheimer's disease, attention-deficit hyperactivity disorder, schizophrenia, epilepsy, central convulsion, eating disorders, obesity, diabetes, hyperlipidemia, sleep disorders, narcolepsy, sleep apnea syndrome, circadian rhythm disorder, depression, allergic rhinitis or other diseases. The present invention is expected to make a great contribution to the development of the pharmaceutical industry.

The invention claimed is:

1. A dihydroquinolinone derivative represented by formula (1) or a pharmaceutically acceptable salt thereof:

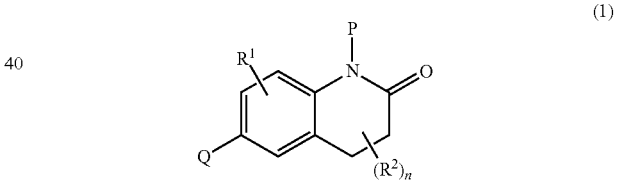

(1)

wherein Q represents the following formula (A) or (B):

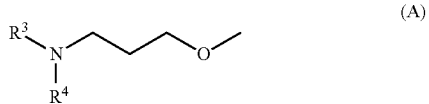

(A)

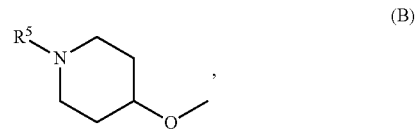

(B)

R$^1$ represents a hydrogen atom, a halogen atom or C$_1$-C$_6$ alkyl,

R$^2$ represents a hydrogen atom or C$_1$-C$_6$ alkyl, n represents 1 or 2,

R$^3$ and R$^4$, which may be the same or different, each represent C$_1$-C$_6$ alkyl or C$_3$-C$_7$ cycloalkyl, or R$^3$ and R$^4$ are attached to each other together with their adjacent nitrogen atom to form a 3- to 7-membered saturated heterocyclic ring (wherein said saturated heterocyclic ring may be substituted with one or two $C_1$-$C_6$ alkyls), $R^5$ represents $C_1$-$C_6$ alkyl (wherein said $C_1$-$C_6$ alkyl may be substituted with one or two $C_3$-$C_7$ cycloalkyls) or $C_3$-$C_7$ cycloalkyl (wherein said $C_3$-$C_7$ cycloalkyl may be substituted with one or two $C_1$-$C_6$ alkyls), and P represents aryl, heteroaryl or heterocyclyl wherein said aryl, heteroaryl or heterocyclyl may be substituted with the same or different 1 to 3 substituents selected from the group consisting of:
- a halogen atom,
- $C_1$-$C_6$ alkyl (wherein said $C_1$-$C_6$ alkyl may be substituted with 1 to 3 halogen atoms, hydroxys, $C_1$-$C_6$ alkoxys or $C_2$-$C_{12}$ dialkylaminos),
- $C_1$-$C_6$ alkoxy (wherein said $C_1$-$C_6$ alkoxy may be substituted with 1 to 3 halogen atoms),
- amino,
- $C_1$-$C_6$ alkylamino,
- $C_2$-$C_{12}$ dialkylamino,
- $C_2$-$C_7$ alkanoyl,
- $C_4$-$C_8$ cycloalkylcarbonyl,
- cyano,
- $C_2$-$C_7$ alkoxycarbonyl,
- $C_2$-$C_7$ alkylaminocarbonyl,
- $C_3$-$C_{13}$ dialkylaminocarbonyl,
- carbonyl attached to a monocyclic saturated heterocyclic ring which contains one or more nitrogen atoms in the ring and may further contain an oxygen or sulfur atom,
- carbamoyl,
- heteroaryl,
- heterocyclyl (wherein said heterocyclyl may be substituted with one or two $C_1$-$C_6$ alkyls), and
- heteroaryloxy (wherein said heteroaryloxy may be substituted with one or two $C_1$-$C_6$ alkyls).

2. The dihydroquinolinone derivative or pharmaceutically acceptable salt thereof according to claim 1, wherein formula (1) is represented by formula (2):

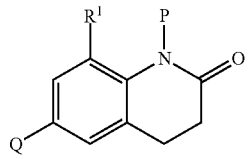

wherein Q, $R^1$ and P are as defined in claim 1.

3. The dihydroquinolinone derivative or pharmaceutically acceptable salt thereof according to claim 1, wherein P represents phenyl, pyridyl, pyrimidinyl, quinolinyl, naphthyridyl, indolyl, 2,3-dihydro[1,4]benzodioxinyl, benzo[1,3]dioxolyl, 2,3-dihydrobenzofuranyl or 2-oxo-1,2-dihydropyridinyl, wherein said phenyl, pyridyl, pyrimidinyl, quinolinyl, naphthyridyl, indolyl, 2,3-dihydro[1,4]benzodioxinyl, benzo[1,3]dioxolyl, 2,3-dihydrobenzofuranyl or 2-oxo-1,2-dihydropyridinyl may be substituted with the same or different 1 to 3 substituents selected from the group consisting of:
- a halogen atom,
- $C_1$-$C_6$ alkyl (wherein said $C_1$-$C_6$ alkyl may be substituted with 1 to 3 halogen atoms, hydroxys, $C_1$-$C_6$ alkoxys or $C_2$-$C_{12}$ dialkylaminos),
- $C_1$-$C_6$ alkoxy (wherein said $C_1$-$C_6$ alkoxy may be substituted with 1 to 3 halogen atoms),
- $C_2$-$C_7$ alkanoyl,
- $C_4$-$C_8$ cycloalkylcarbonyl,
- cyano,
- $C_2$-$C_7$ alkoxycarbonyl,
- $C_2$-$C_7$ alkylaminocarbonyl,
- $C_3$-$C_{13}$ dialkylaminocarbonyl,
- pyrrolidin-1-ylcarbonyl,
- carbamoyl,
- oxazolyl,
- morpholin-4-yl or 2-oxopyrrolidin-1-yl (wherein said morpholin-4-yl or 2-oxopyrrolidin-1-yl may be substituted with one or two $C_1$-$C_6$ alkyls), and
- pyridazinyloxy (wherein said pyridazinyloxy may be substituted with one or two $C_1$-$C_6$ alkyls).

4. A pharmaceutical preparation, which comprises the dihydroquinolinone derivative or pharmaceutically acceptable salt thereof according to claim 1 as an active ingredient.

* * * * *